(12) United States Patent
Nielsen et al.

(10) Patent No.: US 8,298,172 B2
(45) Date of Patent: Oct. 30, 2012

(54) MEDICAL SKIN MOUNTABLE DEVICE AND SYSTEM

(75) Inventors: Ole Christian Nielsen, Hvidovre (DK); Jim Radmer, Fredensborg (DK); Jan Harald Preuthun, Brønshøj (DK); Erik Winkel Ethelfeld, Copenhagen K (DK); Simon Rorvig, Copenhagen (DK); Henrik Bengtsson, Taastrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 46 days.

(21) Appl. No.: 11/911,213

(22) PCT Filed: Apr. 7, 2006

(86) PCT No.: PCT/EP2006/061444
§ 371 (c)(1),
(2), (4) Date: Jan. 3, 2008

(87) PCT Pub. No.: WO2006/108809
PCT Pub. Date: Oct. 19, 2006

(65) Prior Publication Data
US 2009/0131860 A1    May 21, 2009

Related U.S. Application Data

(60) Provisional application No. 60/670,754, filed on Apr. 13, 2005.

(30) Foreign Application Priority Data

Apr. 13, 2005   (DK) ................................ 2005 00526

(51) Int. Cl.
*A61M 31/00* (2006.01)

(52) U.S. Cl. ................ 604/65; 604/66; 604/67

(58) Field of Classification Search ............... 604/65, 604/66, 67, 132, 133
See application file for complete search history.

(56) References Cited

U.S. PATENT DOCUMENTS 2,605,765 A    8/1952   Kollsman
(Continued)

FOREIGN PATENT DOCUMENTS

DE    25 52 446 A1    5/1977
(Continued)

OTHER PUBLICATIONS

Office Action issued in connection with counterpart Danish Application No. PA 2005 00526, mailed Jan. 30, 2006.
(Continued)

*Primary Examiner* — Nicholas Lucchesi
*Assistant Examiner* — Gerald Landry, II
(74) *Attorney, Agent, or Firm* — Wesley A. Nicholas

(57) ABSTRACT

A medical device is provided comprising a transcutaneous device unit and a process unit. The transcutaneous device unit may comprise a transcutaneous device for transporting a fluid through a skin portion of a subject, and a mounting surface adapted for application to the skin of the subject. The process unit may comprise a reservoir adapted to contain a fluid drug, the reservoir comprising an outlet means allowing the transcutaneous device to be arranged in fluid communication with an interior of the reservoir, and an expelling assembly for expelling a fluid drug out of the reservoir and through the skin of the subject via the transcutaneous device. The transcutaneous device unit and the process unit further comprise coupling means allowing the reservoir unit to be secured to the transcutaneous device unit in the situation of use. By this arrangement a two-unit system is provided which can be used in a convenient and cost-effective manner.

12 Claims, 23 Drawing Sheets

U.S. PATENT DOCUMENTS

| | | | |
|---|---|---|---|
| 3,406,686 A | | 10/1968 | Keller |
| 4,077,405 A | | 3/1978 | Haerten et al. |
| 4,140,117 A | | 2/1979 | Buckles et al. |
| 4,201,207 A | | 5/1980 | Buckles et al. |
| 4,340,048 A | | 7/1982 | Eckenhoff |
| 4,468,221 A | | 8/1984 | Mayfield |
| 4,552,561 A | | 11/1985 | Eckenhoff et al. |
| 4,562,751 A | | 1/1986 | Nason et al. |
| 4,685,903 A | | 8/1987 | Cable et al. |
| 4,811,845 A | | 3/1989 | Baggett |
| 4,886,499 A | | 12/1989 | Cirelli et al. |
| 4,898,582 A | | 2/1990 | Faste |
| 5,169,390 A | | 12/1992 | Athayde et al. |
| 5,256,157 A | | 10/1993 | Samiotes et al. |
| 5,257,980 A | | 11/1993 | Van Antwerp et al. |
| 5,487,738 A | | 1/1996 | Sciulli |
| 5,527,288 A | | 6/1996 | Gross et al. |
| 5,568,806 A | | 10/1996 | Cheney, II et al. |
| 5,665,065 A | | 9/1997 | Colman et al. |
| 5,814,020 A | | 9/1998 | Gross |
| 5,858,001 A | | 1/1999 | Tsals et al. |
| 5,896,989 A | | 4/1999 | Ropiak et al. |
| 5,954,643 A | * | 9/1999 | VanAntwerp et al. ........ 600/316 |
| 5,957,895 A | * | 9/1999 | Sage et al. .................. 604/181 |
| 5,961,492 A | | 10/1999 | Kriesel et al. |
| 5,984,894 A | | 11/1999 | Poulsen et al. |
| 5,997,501 A | * | 12/1999 | Gross et al. ..................... 604/65 |
| 6,045,534 A | | 4/2000 | Jacobsen et al. |
| 6,068,613 A | | 5/2000 | Kriesel et al. |
| 6,074,369 A | * | 6/2000 | Sage et al. .................. 604/181 |
| 6,200,293 B1 | * | 3/2001 | Kriesel et al. ................ 604/132 |
| 6,248,093 B1 | | 6/2001 | Moberg |
| 6,251,098 B1 | | 6/2001 | Rake et al. |
| 6,280,148 B1 | | 8/2001 | Zengerle et al. |
| 6,287,289 B1 | | 9/2001 | Niedospial, Jr. |
| 6,290,678 B1 | | 9/2001 | Aydellotte et al. |
| 6,302,869 B1 | | 10/2001 | Klitgaard |
| 6,364,865 B1 | | 4/2002 | Lavi et al. |
| 6,485,471 B1 | | 11/2002 | Zivitz et al. |
| 6,500,150 B1 | | 12/2002 | Gross et al. |
| 6,554,798 B1 | | 4/2003 | Mann et al. |
| 6,589,229 B1 | * | 7/2003 | Connelly et al. ........... 604/890.1 |
| 6,589,369 B2 | * | 7/2003 | Yokoi et al. .................. 148/320 |
| 6,622,037 B2 | | 9/2003 | Kasano |
| 6,764,567 B2 | | 7/2004 | Sperko et al. |
| 6,809,653 B1 | | 10/2004 | Mann et al. |
| 7,250,037 B2 | * | 7/2007 | Shermer et al. ............... 604/134 |
| 2002/0040208 A1 | | 4/2002 | Flaherty et al. |
| 2002/0169416 A1 | * | 11/2002 | Gonnelli et al. ............. 604/142 |
| 2002/0169439 A1 | * | 11/2002 | Flaherty ...................... 604/891.1 |
| 2002/0173769 A1 | * | 11/2002 | Gray et al. .................. 604/506 |
| 2003/0088238 A1 | * | 5/2003 | Poulsen et al. ............. 604/890.1 |
| 2003/0135159 A1 | * | 7/2003 | Daily et al. .................. 604/141 |
| 2003/0163090 A1 | | 8/2003 | Blomquist et al. |
| 2003/0216686 A1 | * | 11/2003 | Lynch et al. ................ 604/93.01 |
| 2004/0059316 A1 | | 3/2004 | Smedegaard |
| 2004/0068230 A1 | | 4/2004 | Estes et al. |
| 2004/0092873 A1 | | 5/2004 | Moberg |
| 2004/0122353 A1 | | 6/2004 | Shahmirian et al. |
| 2004/0138612 A1 | * | 7/2004 | Shermer et al. ........... 604/93.01 |
| 2005/0022274 A1 | | 1/2005 | Campbell et al. |
| 2005/0065760 A1 | | 3/2005 | Murtfeldt et al. |
| 2005/0075670 A1 | * | 4/2005 | Bengtsson ........................ 607/3 |
| 2005/0277884 A1 | | 12/2005 | Kriesel et al. |
| 2007/0088268 A1 | | 4/2007 | Edwards |

FOREIGN PATENT DOCUMENTS

| | | |
|---|---|---|
| DE | 25 52 446 C3 | 5/1977 |
| DE | 4120267 | 12/1992 |
| EP | 1 177 802 A1 | 2/2002 |
| EP | 1 177 802 B1 | 2/2002 |
| EP | 1396275 | 3/2004 |
| EP | 1527792 | 5/2005 |
| EP | 1682203 | 5/2005 |
| EP | 1646412 | 4/2006 |
| EP | 1633414 | 4/2008 |
| JP | 2002-529204 | 9/2002 |
| WO | WO92/22338 | 12/1992 |
| WO | WO 96/14026 A1 | 5/1996 |
| WO | WO0158506 | 8/2001 |
| WO | WO0240083 | 5/2002 |
| WO | WO0241999 | 5/2002 |
| WO | WO0029049 | 9/2002 |
| WO | WO02094352 | 11/2002 |
| WO | WO 03/026726 A1 | 4/2003 |
| WO | WO 03/037403 A1 | 5/2003 |
| WO | WO 2004/056412 A2 | 7/2004 |
| WO | WO2004110526 | 12/2004 |
| WO | WO 2005/002649 A1 | 1/2005 |
| WO | WO 2005/011779 A1 | 2/2005 |
| WO | WO2005039673 | 5/2005 |
| WO | WO2005072795 | 8/2005 |
| WO | WO2005077438 | 8/2005 |

OTHER PUBLICATIONS

International Search Report and Written Opinion issued in connection with counterpart International Application No. PCT/EP2006/061444, mailed Aug. 9, 2006.

International Preliminary Examination Report issued in connection with counterpart PCT Application No. PCT/EP2006/061444, mailed Oct. 25, 2007.

U.S. Appl. No. 60/518,836, filed Nov. 10, 2003, Nielsen et al.

Non-Final Office Action Mailed Dec. 19, 2008 for U.S. Appl. No. 11/411,081, filed April 25, 2006; First Named Inventor: Ole Christian Nielsen.

Notice of Allowance Mailed Jul. 17, 2009 for U.S. Appl. No. 11/411,081, filed April 25, 2006; First Named Inventor: Ole Christian Nielsen.

Notice of Allowance Mailed May 28, 2010 for U.S. Appl. No. 11/411,081, filed April 25, 2006; First Named Inventor: Ole Christian Nielsen.

Notice of Allowance Mailed Aug. 25, 2010 for U.S. Appl. No. 11/411,081, filed April 25, 2006; First Named Inventor: Ole Christian Nielsen.

Non-Final Office Action Mailed Apr. 30, 2010 for U.S. Appl. No. 12/579,169, filed October 14, 2009; First Named Inventor: Ole Christian Nielsen.

Final Office Action Mailed Sep. 14, 2010 for U.S. Appl. No. 12/579,169, filed October 14, 2009; First Named Inventor: Ole Christian Nielsen.

Non-Final Office Action Mailed Apr. 10, 2009 for U.S. Appl. No. 12/066,712, filed March 13, 2008; First Named Inventor: Ole Christian Nielsen.

Non-Final Office Action Mailed Oct. 27, 2009 for U.S. Appl. No. 12/066,712, filed March 13, 2008; First Named Inventor: Ole Christian Nielsen.

Final Office Action Mailed Apr. 28, 2010 for U.S. Appl. No. 12/066,712, filed March 13, 2008; First Named Inventor: Ole Christian Nielsen.

Office Action Mailed Aug. 23, 2010 in U.S. Appl. No. 12/090,499, filed April 17, 2008; First Named Inventor: Karsten Kallesoe Nielsen.

English Abstract of JP2002-592204 Filed Sep. 10, 2002.

English Abstract of DE 4120267, Apr. 13, 2005.

* cited by examiner

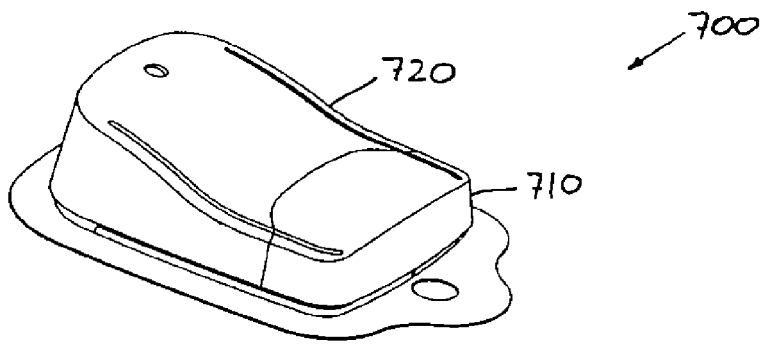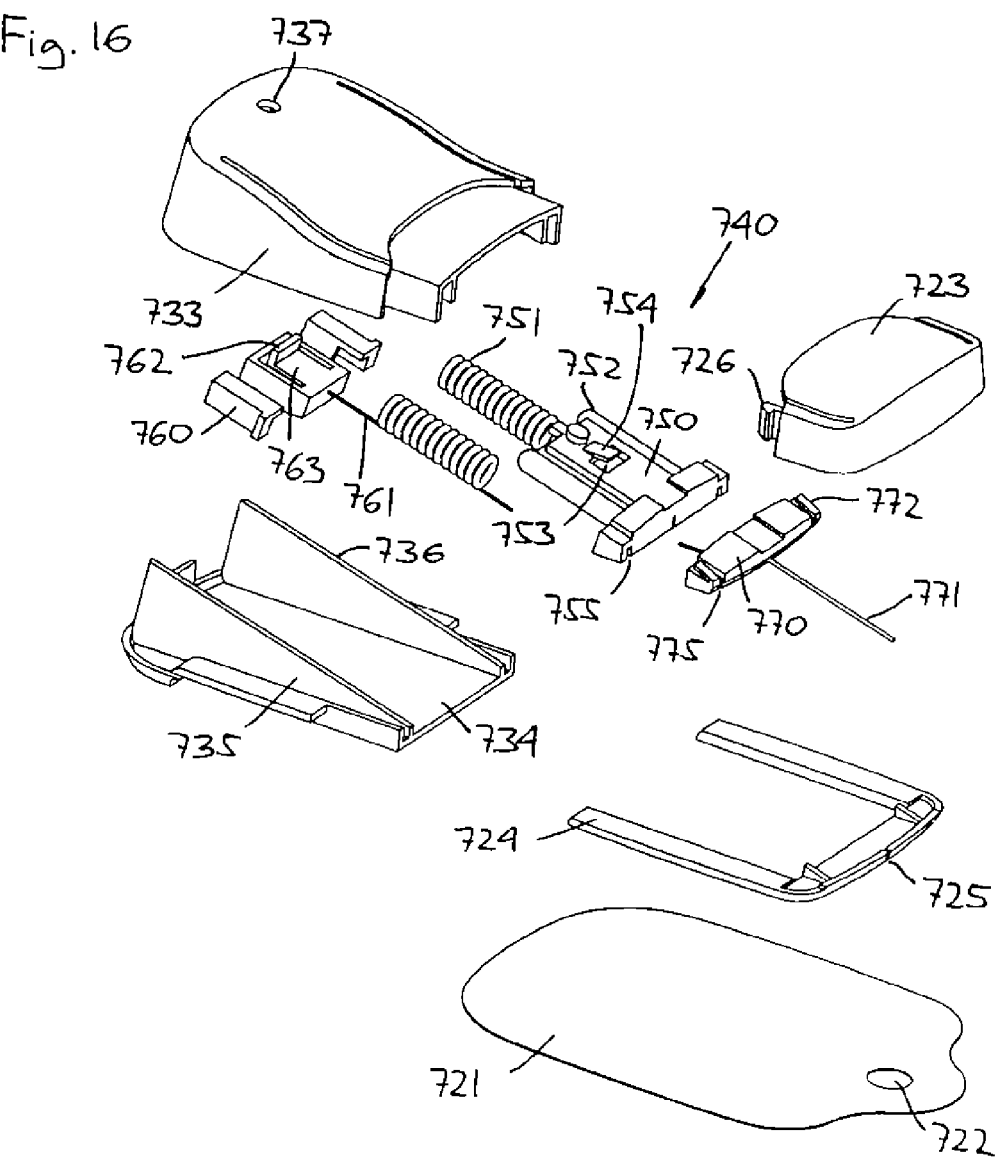

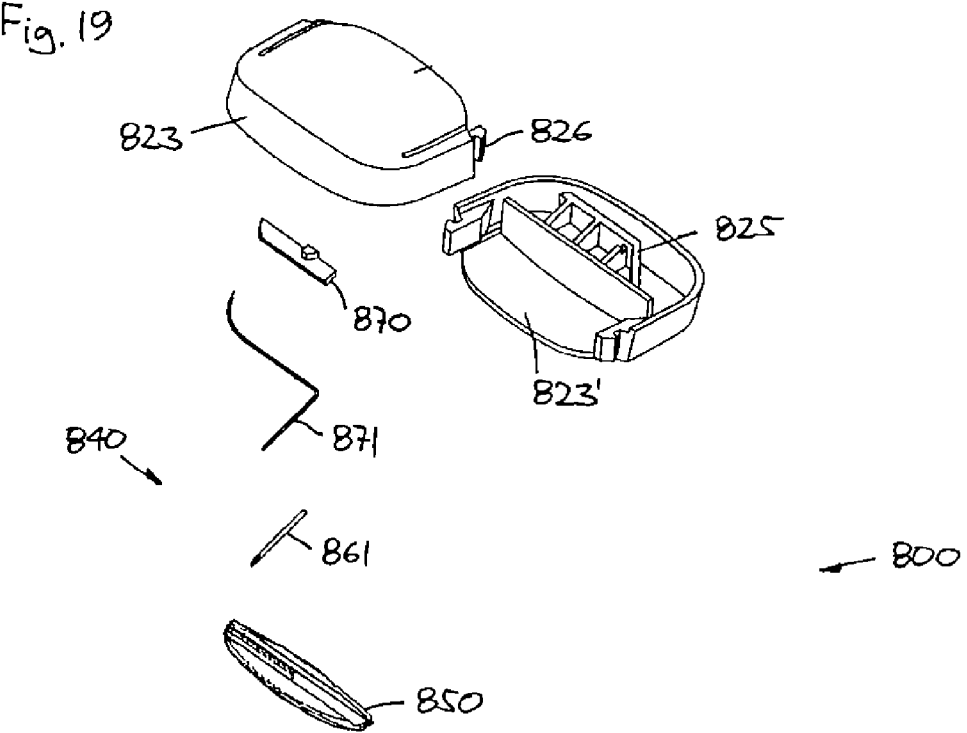
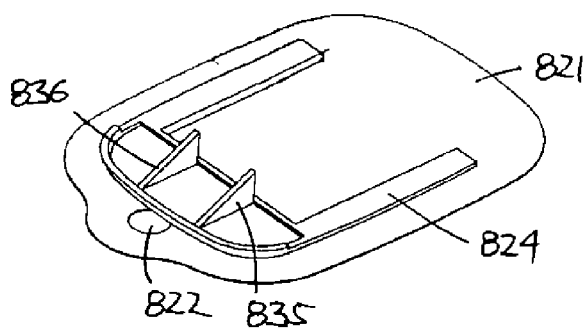
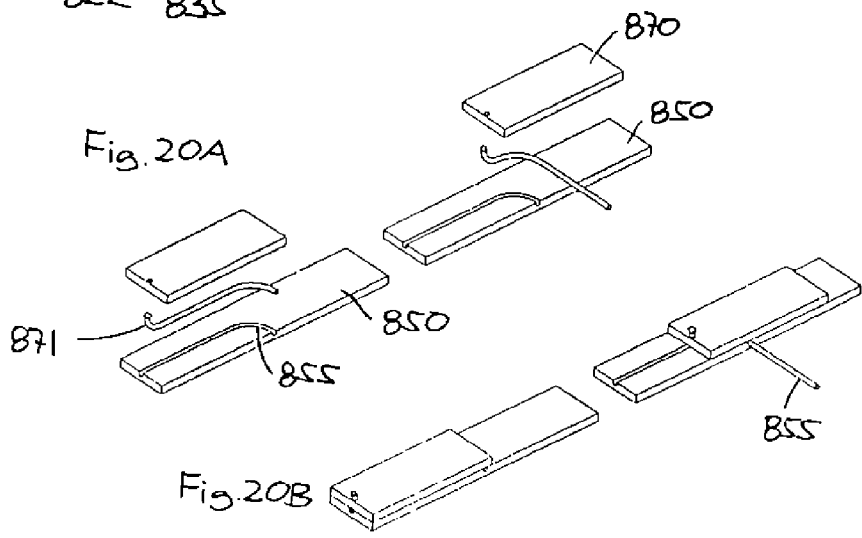

MEDICAL SKIN MOUNTABLE DEVICE AND SYSTEM

CROSS-REFERENCE TO RELATED APPLICATIONS

This application is a 35 U.S.C. §371 national stage application of International Patent Application PCT/EP2006/061444 (published as WO 2006/108809), filed Apr. 7, 2006, which claimed priority of Danish Patent Application PA 2005 00526, filed Apr. 13, 2005; this application further claims priority under 35 U.S.C. §119 of U.S. Provisional Application 60/670,754, filed Apr. 13, 2005.

The present invention generally relates to devices which are adapted for application to a skin surface of a subject and comprise a transcutaneous device which can be used for e.g. introduction of a fluid through the skin of the subject or as a sensor. In specific aspects, such devices may comprise a reservoir adapted to contain a fluid drug, and expelling means for expelling fluid drug out of the reservoir and through the skin of the subject via the transcutaneous device.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference. U.S. Pat. No. 6,364,865 discloses a manually held infusion device allowing two vial-type containers to be connected and a pressure to be build up in one of the containers to thereby expel a drug contained in that container.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use. The infusion needle may be arranged to permanently project from the mounting surface such that the needle is inserted simultaneously with the application of the infusion pump, this as disclosed in U.S. Pat. Nos. 2,605,765, 4,340,048 and in EP 1 177 802, or the needle may be supplied with the device in a retracted state, i.e. with the distal pointed end of the needle "hidden" inside the pump device, this allowing the user to place the pump device on the skin without the possibility of observing the needle, this as disclosed in U.S. Pat. Nos. 5,858,001 and 5,814,020. In addition to pumps, alternative means for transporting a fluid drug may be used, e.g. iontophoresis as discussed below.

Although it can be expected that the above described second class of fully or partly disposable infusion devices can be manufactured considerably cheaper than the traditional durable infusion pump, they are still believed to be too expensive to be used as a real alternative to traditional infusion pumps for use on an every-day basis.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned primarily with devices comprising a transcutaneous device such as a needle-formed sensor element.

The sensor may be placed subcutaneously being connected to external equipment by wiring or the substance (e.g. fluid) to be analysed may be transported to an external sensor element, both arrangements requiring the placement of a subcutaneous component (e.g. small catheter or tubing), the present invention addressing both arrangements. However, for simplicity the term "sensor" is used in the following for both types of elements introduced into the subject.

DISCLOSURE OF THE INVENTION

Having regard to the above-identified problems, it is an object of the present invention to provide a skin mountable drug delivery device or system and components therefore, which allow such a device or system to be used in a convenient and cost-effective manner. The configuration of the system and the components therefore should contribute in providing a medical delivery means which allows for easy and swift operation yet being reliable in use.

In the disclosure of the present invention, embodiments and aspects will be described which will address one or more of the above objects or which will address objects apparent from the below disclosure as well as from the description of exemplary embodiments.

Thus, corresponding to a first aspect, a medical device comprising a transcutaneous unit and a process unit is provided, wherein the transcutaneous device unit comprises a mounting surface adapted for application to the skin of the subject, and a transcutaneous device comprising a distal end adapted to be inserted through the skin of a subject, the distal end being moveable between an initial position in which the distal end is retracted relative to the mounting surface, and an extended position in which the distal end projects relative to the mounting surface, and wherein the process unit comprises a process assembly adapted to cooperate with the transcutaneous device, wherein the transcutaneous device unit and the process unit are adapted to be secured to each other to form a unitary device. By the term "unitary" is indicated that the two units are not merely physically connected by some kind of "loose" structure such as a flexible wire or a flexible fluid conduit as when connecting a conventional infusion set to a conventional infusion pump.

When it is defined that the two units are adapted to be secured to each other, this also covers the situation in which a portion of the transcutaneous device unit has to be removed prior to securing the process unit. This may e.g. be the case where the transcutaneous device unit comprises a removable inserter portion.

The transcutaneous device unit may be provided with actuation means for moving the distal end of the transcutaneous device between the initial and the extended position when the actuation means is actuated.

The term "process assembly" covers an aggregation of components which are adapted to interact with the transcutaneous device to provide a given functionality. For example, the transcutaneous device may be in the form of a transcutaneous sensor device, and the process assembly comprises a processor adapted to transmit and/or process data acquired via the sensor device.

In another example, the transcutaneous device is in the form of a transcutaneous access device, and the process assembly comprises a reservoir adapted to contain a fluid drug, an expelling assembly adapted for cooperation with the reservoir to expel fluid drug out of the reservoir and through the skin of the subject via the transcutaneous access device, and a processor for controlling the expelling assembly. A transcutaneous device may also be combined with a sensor element to form a combined transcutaneous device. Such a medical device may be used in a system further comprising a remote control unit comprising a processor, the medical device and the remote control unit being adapted to transmit data therebetween. The remote control unit may be adapted to receive externally supplied values and calculate a bolus amount of drug to be infused based upon the externally supplied values, e.g. it may be adapted to calculate a bolus amount of drug to be infused based upon externally supplied values representing material to be ingested by the body of the subject. The system may comprise a first analyte sensor device adapted to provide data indicative of a concentration of the first analyte in the user, the remote control unit comprising an infusion calculator for calculating a bolus or infusion rate on the basis of data supplied by the first analyte sensor. The system may also comprise a second analyte sensor device adapted to provide data indicative of a concentration of the second analyte in the user, the remote control unit comprising an infusion calculator for calculating a bolus or infusion rate on the basis of data supplied by the first and second analyte sensors. The first and second analytes may be blood glucose, in which case the first analyte sensor is a BGM, the second analyte sensor is a CGM, and the remote control unit is adapted to calculate an amount or infusion rate of insulin.

For the different embodiments described above, the medical device or system may comprise releasable mating coupling means for securing the transcutaneous device unit and the process unit to each other to form a substantially rigid connection therebetween.

In a further aspect a system is provided comprising a first transcutaneous device unit and a first process unit as described above, and at least one further transcutaneous device unit being different from the first transcutaneous device unit, whereby each combination of a transcutaneous device unit and a process unit provides different capabilities. Alternatively, a system is provided comprising a first transcutaneous device unit and a first process unit as described above, and at least one further process unit being different from the first process unit, whereby each combination of a transcutaneous device unit and a process unit provides different capabilities.

The term "capabilities" is used to denote a set of actions or functions resulting from a combination of the two units. The different capabilities may be based on structure (e.g. different patch units having different transcutaneous devices) or functionality (e.g. different pump units being programmed to deliver at different infusion rates). In the context of the present application, the term "different capabilities" is also used to indicate that the "potential" capabilities are different, however, in case the capabilities are overlapping, the user may e.g. choose to operate a given pump unit corresponding to the capabilities of another pump unit, or two different pump units may be used in the same way. For example, a pump unit allowing user-programming of infusion profiles as well as a bolus function may be used to activate a simple constant flow rate corresponding to the capabilities of a simple pump unit.

The present invention also provides a method of using the components comprising the steps of (i) providing a transcutaneous device unit comprising a transcutaneous device and a mounting surface, the transcutaneous device having retracted position relative to the mounting surface, and an extended position in which a distal end projects relative to the mounting surface, (ii) providing a process unit comprising a process assembly adapted to cooperate with the transcutaneous device, (iii) mounting the mounting surface to a skin surface of a subject, (iv) inserting the transcutaneous device into the subject by moving the transcutaneous device from the retracted position to the extended position, and (v) assembling the transcutaneous device unit and the process unit to provide a functional communication between the process assembly and the inserted transcutaneous device. The insertion step may take place after the assembling step, just as the insertion may be automatically activated when the two units are assembled. Alternatively, the two units may be assembled before they are mounted to the skin surface and the transcutaneous device inserted.

Corresponding to a further aspect, a medical device comprising a transcutaneous unit and a reservoir unit is provided, wherein the transcutaneous unit comprises transcutaneous means for transporting a fluid through a skin portion of a subject, and a mounting surface adapted for application to the skin of the subject. The reservoir unit comprises a reservoir adapted to contain a fluid drug, the reservoir comprising an outlet allowing the transcutaneous means to be arranged in fluid communication with an interior of the reservoir, and expelling means for, in a situation of use, expelling a fluid drug out of the reservoir and through the skin of the subject via the transcutaneous means. The transcutaneous unit and the reservoir unit further comprise coupling means allowing the reservoir unit to be secured to the transcutaneous unit in the situation of use.

The term "transcutaneous" covers all forms of administration in which a fluid is transported through a portion of the skin, e.g. intradermal or subcutaneous administration. The transcutaneous means may be in the form of a transcutaneous device, a jet injection means or electrodes allowing an ionic agent to permeate from a predetermined site on the surface of skin into the subcutaneous tissue of the subject by using the principle of iontophoresis. For a more thorough discussion of iontophoresis reference is made to U.S. Pat. No. 6,622,037 hereby incorporated by reference. Depending on the nature of the transcutaneous means the expelling means may be of different configuration and nature. For example, when one or more hollow infusion needles or cannulas are used, the expelling means may be arranged to force or suck the fluid drug from the reservoir, whereas in the case of iontophoresis the expelling means would be means for applying a current over a set of electrodes, i.e. "driving" means.

Corresponding to a further aspect, a medical device comprising a transcutaneous device unit and a reservoir unit is provided, wherein the transcutaneous device unit comprises a transcutaneous device, and a mounting surface for application to the skin of the subject. The reservoir unit comprises a reservoir adapted to contain a fluid drug, and an expelling assembly adapted for cooperation with the reservoir to expel the fluid drug out of the reservoir and through the skin of the subject via the transcutaneous device. The transcutaneous device unit and the reservoir unit are further adapted to be secured to each other in a situation of use thereby allowing a fluid communication to be established between the reservoir and the transcutaneous device. The transcutaneous device unit and the reservoir unit may comprise releasable coupling means allowing the reservoir unit to be secured to the transcutaneous device unit in a situation of us. Such a medical device comprising two units may also be considered a medical system. The transcutaneous device unit and the reservoir unit may each comprise a housing within which the transcutaneous device respectively the reservoir and the expelling assembly are arranged.

The term expelling assembly covers an aggregation of components or structures which in combination provides that a fluid can be expelled from the reservoir. The expelling assembly may e.g. be a mechanical pump (e.g. a membrane pump, a piston pump or a roller pump) in combination with electronically controlled actuation means, a mechanically driven pump (e.g. driven by a spring), a gas driven pump or a pump driven by an osmotic engine. The expelling assembly may also be in the form of an aggregation of components or structures which in combination provides that a fluid can be expelled from the reservoir when the expelling assembly is controlled or actuated by a controller external to the expelling assembly.

The transcutaneous device (which term also covers the similar terms transcutaneous access device and transcutaneous access tool traditionally used in this technical field) may be in the form of a pointed hollow infusion needle, a micro needle array, or a relatively flexible per se blunt cannula (or sensor) may be provided in combination with a pointed insertion needle, the insertion needle being retractable after insertion of the blunt portion of the transcutaneous device. The term "transcutaneous device" may also be used to denote such a combination although only a part of it is adapted to be inserted for an extended period of time. The cannula is advantageously soft and flexible relative to the insertion needle which typically is a solid steel needle. Especially when the transcutaneous device is in the form of a rigid needle it may be advantageous to provide retraction means for such a needle. In the disclosure of the present invention as well as in the description of the exemplary embodiments, reference will mostly be made to a transcutaneous device in the form of an infusion needle or cannula. The length of the transcutaneous device may be chosen in accordance with the actual application, e.g. a hollow steel needle which may be inserted at a substantially right angle relative to the skin surface may have an inserted length of 2-8 mm, preferably 3-5 mm, whereas a cannula which may also be inserted at an oblique angle relative to the skin cannula which may also be inserted at an oblique angle relative to the skin surface may be somewhat longer, e.g. 4-20 mm.

In an exemplary embodiment the insertion needle is a hollow needle arranged coaxially with and outside the transcutaneous device and being axially moveable relative thereto, the needle comprising a distal portion adapted to penetrate the skin of the subject, wherein the medical device is transformable between (a) a first state in which the transcutaneous device and the needle are retracted relative to the mounting surface, (b) a second state in which the transcutaneous device and the needle are extended relative to the mounting surface with the distal end of the needle projecting relative to the distal portion of the transcutaneous device thereby allowing the transcutaneous device to be introduced through the skin of the subject, and (c) a third state in which the distal end of the needle is retracted relative to the distal portion of the transcutaneous device. The process unit may be adapted to be releasably coupled to the transcutaneous device unit thereby, in a situation of use, substantially covering an introduction site of the transcutaneous device through the skin, wherein at least partial removal of the process unit from the transcutaneous device unit at least partially uncovers the introduction site.

The mounting surface is adapted for application against the skin of a subject (e.g. user or patient) and may be held in contact with the skin by attaching means external to the mounting surface (e.g. coupling means allowing the medical device to be coupled to a skin mountable device, or an adhesive bandage or a dressing) or by adhesive means provided on the mounting surface. The mounting surface may also be adapted for mounting towards the skin via an interposed component of a skin mountable device, e.g. a skin mountable device may comprise a receiving portion to which the medical device is attached, the transcutaneous device being inserted into the skin through an aperture in the receiving portion.

By the above arrangement different concepts can be realized. For example, by providing at least two different of one of the units, it will be possible to provided two or more combinations, wherein each combination of a transcutaneous device unit and a reservoir unit provides an assembly will have different capabilities as discussed in further detail below. In case the units are provided with releasable coupling means, one of the units can be exchanged with a new or different unit yet allowing the other unit to be re-used, thereby lengthening the operational life of the re-used unit. Thus, the present invention provides in an exemplary embodiment a device in which the components providing the interface with the user is incorporated in a first unit whereas the components providing the drug delivery per se is incorporated in a second unit, this allowing the combined components to be combined or exchanged in a simple, reliable and user-friendly way.

For example, the reservoir unit may be provided with an amount of drug and a delivery pump comprising an energy source allowing the drug to be delivered over e.g. 10 days, whereas the transcutaneous device unit may be provided with a transcutaneous device and an adhesive surface on the mounting surface having an expected (or recommended) operational life of 2 days, this allowing the reservoir unit to be used with 5 transcutaneous device units over a period of 10 days, this considerably lowering the total costs of using the combined device. The reservoir may be pre-filled or adapted to be filled one or more times.

On the other hand, a transcutaneous device unit may be provided with e.g. a needle or a soft cannula, and adhesive means (e.g. of the type used for attaching colostomy bags) allowing the needle unit to be mounted and used over an extended period of time, the reservoir unit having a shorter expected operational life, e.g. when relatively large amounts of drugs have to be infused. Alternatively, different reservoir units with different types of drugs may be used in combination with such a "long-term" mounted needle unit.

For ease of use, the fluid communication between the needle and the reservoir may be established when the needle unit and the reservoir unit are secured to each other, just as the expelling means may be activated when the needle unit and the reservoir unit are secured to each other and de-activated when the units are released from each other. Indeed, one or both of the operations may also be performed manually by the user.

In an exemplary embodiment the expelling assembly comprises a pump having an inlet adapted to be arranged in fluid communication with the outlet of the reservoir, and an outlet adapted to be arranged in fluid communication with the transcutaneous device, thereby allowing the transcutaneous device to be arranged in fluid communication with the interior of the reservoir. By such an arrangement the pump will serve as a suction pump drawing drug from the reservoir which consequently will have to be either collapsible or vented in case a non-collapsible reservoir is used. The expelling assembly may also be in the form of an arrangement adapted to pressurize the reservoir, e.g. an arrangement for driving a piston in a reservoir comprising a displaceable piston. The reservoir unit may comprise more than one reservoir and more than one expelling assembly. For example, a single expelling assembly may be used to expel drug from more than one reservoir, either simultaneously thereby mixing drugs or alternating, or each reservoir may be provided with an expelling assembly which may be connected to a common transcutaneous device or to individual transcutaneous devices, e.g. the transcutaneous device unit may comprise more than one transcutaneous device adapted to be connected to a expelling assembly.

In order to provide an initially sterile flow path through the pump, the flow path may be arranged between the inlet and outlet such that the inlet and outlet seal the interior of the pump and thereby the flow path in an initial sterile state. By this arrangement it will not be necessary to provide the reservoir unit as an entirely sterile unit—indeed, the drug will have to be provided in a sterile state.

In an exemplary embodiment, the reservoir unit is transformable from an initial condition in which there is no fluid communication between the pump and the reservoir to a non-reversible operating condition in which fluid communication is established between the inlet means of the pump and the outlet means of the reservoir when the pump unit is secured to a needle unit for the first time. By this arrangement it is avoided that undesired matter is introduced into the reservoir during re-connection between the pump and the reservoir.

To secure a clean connection between the pump and the reservoir, a separate fluid connector may be arranged within the interior of the pump in the initial condition. Such a fluid connector may comprise a pointed inlet end and an outlet, whereas the inlet of the pump and the outlet of the reservoir may be in the form of two needle-penetratable septa. By this arrangement the pointed end of the fluid connector, e.g. a connection needle, can be moved through the two septa and thus between the initial condition and an operating condition in which fluid communication is established between the interior of the reservoir and the interior of the pump via the fluid connector, the outlet of the fluid connector being arranged in the flow path. Advantageously the fluid connector is moved between its two positions as the reservoir unit is connected to a transcutaneous device unit for the first time. Correspondingly, during such a first connection two fluid communications will be established (between the transcutaneous device of the transcutaneous device and the pump, and between the pump and the reservoir), whereas during subsequent connections only a single new fluid communication will be established (between the transcutaneous device of the transcutaneous device unit and the pump).

In an exemplary embodiment the transcutaneous device comprises a first portion having a pointed distal end, and a second portion in fluid communication with the first portion and having a second end. Advantageously the second end of the transcutaneous device is pointed and the outlet means of the pump comprises a needle-penetratable septum allowing a fluid communication to be established between the second end of the transcutaneous device and the interior of the pump, preferably as the two units are connected to each other.

Correspondingly, in a further aspect the present invention provides a pump having an inlet means adapted to be arranged in fluid communication with a fluid supply, and an outlet means, the pump comprising an internal flow path arranged between the inlet and outlet means, the inlet and outlet means sealing the interior of the pump and thereby the flow path in an initial sterile condition, wherein a fluid connection means is arranged within the interior of the pump in the initial condition, the fluid connection means comprising an inlet end and an outlet, whereby the fluid connection means is arranged to be moved between the initial condition and to an operating condition in which the inlet end projects from the pump inlet means, whereby a fluid communication can be established between the fluid supply and the interior of the pump via the fluid connection means and with the outlet of the fluid connection means being arranged in the flow path.

The transcutaneous device unit may be supplied with e.g. a needle projecting from the mounting surface, however, to limit the risk of accidental needle injuries, the distal end of the transcutaneous device is advantageously moveable between an initial position in which the distal end is retracted relative to the mounting surface, and an extended position in which the distal end projects relative to the mounting surface. Depending on the intended method of mounting the device on the user, the transcutaneous device may be moved between the two positions as the two units are connected to each, as would be appropriate in case the transcutaneous device unit is mounted on the skin of the user before the reservoir unit is connected. However, in case the two units are intended to be connected to each other before assembled units are mounted on the skin of the user, the transcutaneous device unit advantageously comprises user-actuatable actuation means for moving the pointed end of the transcutaneous device between the initial and the extended position.

To prevent inadvertent actuation of the transcutaneous device before the two units are assembled, the transcutaneous device unit may comprise means for blocking the actuation means, the blocking means being released when the transcutaneous device unit and the reservoir unit are secured to each other, thereby allowing the actuation means to be actuated.

To further reduce the likelihood of transcutaneous device injuries, the distal end of the transcutaneous device may be moveable between the extended position in which the distal end projects relative to the mounting surface, and a retracted position in which the distal end is retracted relative to the mounting surface. Correspondingly, the combined device may comprise user-actuatable retraction means for moving the distal end of the transcutaneous device between the extended and the retracted position when the retraction means is actuated. To prevent re-use of the transcutaneous device, the transcutaneous device may be permanently locked in its retraced position.

To prevent user-errors the actuation means for introducing the transcutaneous device may in an initial condition cover the retraction means, actuation of the actuation means uncovering the retraction means. For example, the actuation means may be in the form of gripping means (e.g. a strip) which is removed from the device, whereby removal triggers transcutaneous device insertion and at the same time uncovers the retraction for withdrawing the transcutaneous device.

As described above, the expelling assembly may be activated and deactivated when the two units are assembled and disassembled, however, the actuation and retraction means may also be used to activate respectively deactivate the expelling assembly. Just as for the initial connection between the pump and the reservoir, the initial activation of the expelling assembly may result in electronic control means being activated resulting in start of pumping action, whereas subsequent deactivation will only deactivate the actual pump action, the control means still being active (e.g. counting the time since initial activation of the control means).

In the above disclosure of the invention the two units have been described primarily as "unitary" units, however, this is only an exemplary configuration and these two "main" units may in case it is deemed desirable be subdivided into further units. For example, the reservoir unit may be provided with an exchangeable control unit, this allowing different types of control units to be connected to the reservoir unit per se. e.g. a first type of control unit may provide a single delivery profile, a second control unit may be programmable to thereby modify the delivery pattern, or a control third unit may comprise means allowing the control unit to communicate with external means. In the latter case the control unit may be controlled using a cordless remote control. Correspondingly, the reservoir may be exchangeable allowing different sizes of reservoirs or different types of drugs to be used.

In a further aspect of the invention, a transcutaneous device unit is provided as described above and being adapted to be used in combination with a reservoir unit as disclosed above. Correspondingly, the invention also provides a reservoir unit as disclosed above, the reservoir unit being adapted to be used in combination with a transcutaneous device unit as disclosed above. In an exemplary embodiment such a transcutaneous device unit may be provided with a hollow needle comprising a pointed distal end with an outlet opening and being adapted to penetrate the skin of a subject, and a pointed proximal end with an inlet opening forming a fluid inlet means, the fluid inlet means being adapted to be arranged in fluid communication with a fluid supply. By this arrangement the needle provides a hydraulically stiff fluid communication between the needle inlet and outlet openings (e.g. made from metal), this allowing early occlusion detection by monitoring a pressure build-up upstream of the needle.

In a yet further aspect, a system is provided comprising a first needle unit and a first reservoir unit as disclosed above in combination with a least one further needle unit or reservoir unit as disclosed above, the further unit(s) having different capabilities than the first units. The different capabilities may relate to any constructional feature of the units, e.g. the type of needle, the type of user-actuatable means, the type of delivery/pump means, or the type of reservoir/drug.

More specifically, in an exemplary embodiment a system is provided comprising a transcutaneous device unit as disclosed above, and a plurality of reservoir units, each comprising a reservoir containing a fluid drug, and an expelling assembly for expelling fluid drug from the reservoir. The transcutaneous device unit and the reservoir units comprise mating coupling means allowing a reservoir unit to be secured to the transcutaneous device unit to provide fluid communication between the reservoir and the transcutaneous device, wherein each combination of a transcutaneous device unit and a reservoir unit provides an assembly having different capabilities. The different capabilities may be realized providing e.g. reservoir units with different amounts of the same drugs, reservoir units with different drugs or variants of a given drug, reservoir units adapted to expel drug at different preset rates, reservoir units adapted to expel at fixed respectively selectable rates. One of the reservoir units may be provided with a processor controlling the expelling assembly and a receiver operatable coupled to the controller for receiving flow instructions from a separate control device and delivering the flow instructions to the processor. The receiver may be a wireless receiver. The reservoir units may further be provided with different input means (e.g. for wireless or non-wireless connection, or manual input), or different output means (e.g. for wireless or non-wireless connection, different display means, or different alarm means).

In a further exemplary embodiment, a system is provided comprising a plurality of transcutaneous device units as described above, and a reservoir unit comprising a reservoir containing a fluid drug, and an expelling assembly for expelling fluid drug from the reservoir. The transcutaneous device units and the reservoir unit comprise mating coupling means allowing a transcutaneous device unit to be secured to the reservoir unit to provide fluid communication between the reservoir and the transcutaneous device, wherein each combination of a transcutaneous device unit and a reservoir unit provides an assembly having different capabilities. The different capabilities may be realized by providing the transcutaneous device units with different transcutaneous devices such as a hollow subcutaneous needle, a cannula and insertion needle assembly, and a micro needle array, by providing different adhesives, by providing different insertion or retraction means, or by providing different coupling means.

In a yet further exemplary embodiment, a system is provided comprising a transcutaneous device unit comprising a transcutaneous device and a mounting surface adapted for application to the skin of a subject, a reservoir unit comprising a reservoir containing a fluid drug, and at least a portion of an expelling assembly for expelling fluid drug from the reservoir, and a plurality of control units, each comprising a controller for controlling an expelling assembly, each having different capabilities. The transcutaneous device unit and the reservoir unit comprise mating coupling means allowing the reservoir unit to be secured to the transcutaneous device unit to provide fluid communication between the reservoir and the transcutaneous device, and the controller units and the reservoir unit comprise mating coupling means allowing a controller unit to be secured to the reservoir unit to control the expelling assembly, whereby each combination of a transcutaneous device unit, a reservoir unit and a control unit provides an assembly having different capabilities. The control units may have different control functions as described above in respect of a system comprising a plurality of reservoir units. In an alternative configuration the reservoir unit and the transcutaneous device unit may be provided as a unitary structure adapted to cooperate with the control unit.

The present invention also provides a method comprising the steps of providing a transcutaneous device unit comprising a transcutaneous device and a mounting surface, providing a reservoir unit comprising a reservoir adapted to contain a fluid drug, and an expelling assembly for expelling fluid drug from the reservoir, the method comprising the further step of assembling the transcutaneous device unit and the reservoir unit to provide a fluid communication between the reservoir and the transcutaneous device. The fluid communication between the transcutaneous device and the reservoir may be established when the two units are assembled or it may be established when the assembled device is further actuated, both options being covered by the above definition. The method may comprise the further steps of mounting the mounting surface to a skin surface of a subject, and, after mounting the mounting surface to the skin surface of the subject, actuating the transcutaneous device to establish a fluid communication between the reservoir and the subject.

A further method provides a drug delivery device dispensing a drug at a preset rate, the method comprising the steps of providing a system comprising a transcutaneous device unit comprising a transcutaneous device and a mounting surface adapted for application to the skin of a subject, the system further comprising a plurality of reservoir units, each comprising a reservoir containing a fluid drug, and an expelling assembly for expelling fluid drug from the reservoir at a preset rate, selecting a reservoir unit having a desired preset rate, and assembling the transcutaneous device unit and the selected reservoir unit to provide a fluid communication between the reservoir and the transcutaneous device.

In the above disclosure the present invention has been described with reference to a drug delivery device, however, the concept of the invention can be regarded as a modular system providing a number of advantages. Thus, the transcutaneous device unit may also be in the form of a needle sensor and the "reservoir unit" may correspondingly be in the form of a device adapted to transmit and/or process data acquired via the sensor.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein FIG. 15 shows medical device comprising a patch unit and an inserter unit, FIG. 16 shows an exploded view of the device of FIG. 15, FIG. 19 shows an exploded view of a patch unit comprising an inserter assembly, FIG. 20A shows in an exploded view details of the inserter assembly of FIG. 19, FIG. 20B shows the details of FIG. 20A in an assembled state.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Firstly, with reference to FIGS. 1-3 an embodiment of a medical device for drug delivery will be described focusing primarily on the directly user-oriented features. The transcutaneous device unit 2 comprises a transcutaneous device in the form of a hollow infusion device, e.g. a needle or soft cannula, and will thus in the following be termed a needle unit, however, the needle may be replaced with any desirable transcutaneous device suitable for delivery of a fluid drug or for sensing a body parameter.

Figure 1:
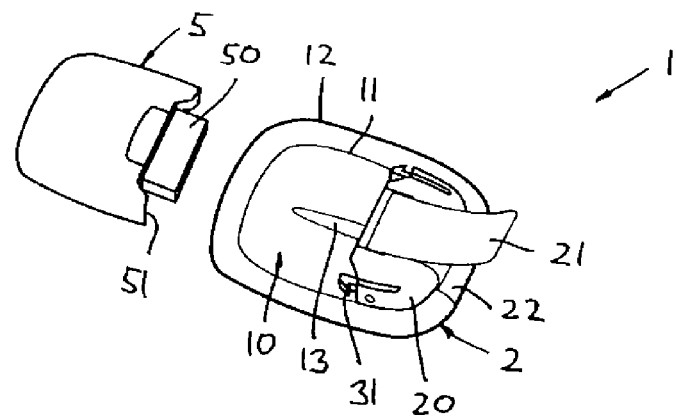
FIGS. 1-3 shows in perspective views sequences of use for a first embodiment of a drug delivery device.

More specifically, FIG. 1 shows a perspective view of medical device in the form of a modular skin-mountable drug delivery device 1 comprising a patch-like needle unit 2 (which may also be denoted a patch unit) and a reservoir unit 5. When supplied to the user each of the units are preferably enclosed in its own sealed package (not shown). The embodiment shown in FIG. 1 comprises a patch unit provided with an insertable steel needle, however, the embodiment is exemplary of how to use a patch unit with an insertable transcutaneous device, e.g. needle, cannula or sensor. In case an actual embodiment requires the patch unit to be mounted on the skin and the transcutaneous device inserted before a reservoir or other unit can be attached, it follows that the method of use would be adopted correspondingly.

The needle unit comprises a flexible patch portion 10 with a lower adhesive mounting surface adapted for application to the skin of a user, and a housing portion 20 in which a hollow infusion needle (not shown) is arranged. The needle comprises a pointed distal end adapted to penetrate the skin of a user, and is adapted to be arranged in fluid communication with the reservoir unit. In the shown embodiment the pointed end of the needle is moveable between an initial position in which the pointed end is retracted relative to the mounting surface, and an extended position in which the pointed end projects relative to the mounting surface. Further, the needle is moveable between the extended position in which the pointed end projects relative to the mounting surface, and a retracted position in which the pointed end is retracted relative to the mounting surface. The needle unit further comprises user-gripable actuation means in the form of a first strip-member 21 for moving the pointed end of the needle between the initial and the second position when the actuation means is actuated, and user-gripable retraction in the form of a second strip-member 22 means for moving the pointed end of the needle between the extended and the retracted position when the retraction means is actuated. As can be seen, the second strip is initially covered by the first strip. The housing further comprises user-actuatable male coupling means 31 in the form of a pair of resiliently arranged hook members adapted to cooperate with corresponding female coupling means on the reservoir unit, this allowing the reservoir unit to be releasable secured to the needle unit in the situation of use. A flexible ridge formed support member 13 extends from the housing and is attached to the upper surface of the patch. In use a peripheral portion 12 of the patch extends from the assembled device as the reservoir unit covers only a portion 11 of the upper surface of the patch. The adhesive surface is supplied to the user with a peelable protective sheet.

The reservoir unit 5 comprises a pre-filled reservoir containing a liquid drug formulation (e.g. insulin) and an expelling assembly for expelling the drug from the reservoir through the needle in a situation of use. The reservoir unit has a generally flat lower surface adapted to be mounted onto the upper surface of the patch portion, and comprises a protruding portion 50 adapted to be received in a corresponding cavity of the housing portion 20 as well as female coupling means 51 adapted to engage the corresponding hook members 31 on the needle unit. The protruding portion provides the interface between the two units and comprises a pump outlet and contact means (not shown) allowing the pump to be started as the two units are assembled. The lower surface also comprises a window (not to be seen) allowing the user to visually control the contents of the reservoir before the two units are connected.

Figure 2:
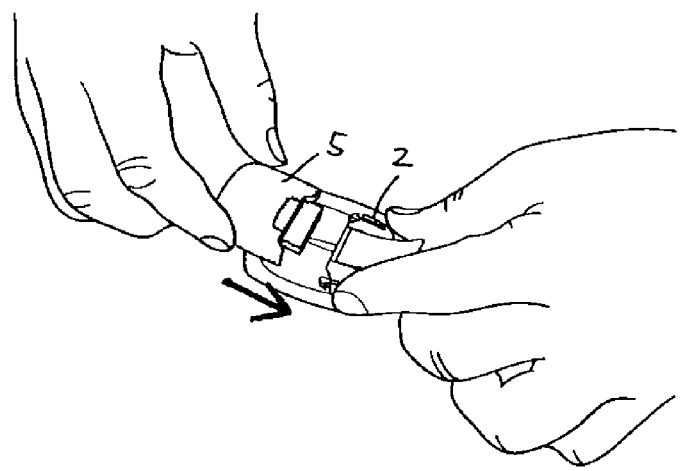

First step in the mounting procedure is to assemble the two units by simply sliding the reservoir unit into engagement with the needle unit (FIG. 2). When the hook members properly engage the reservoir unit a "click" sound is heard (FIG. 3) signalling to the user that the two units have been properly assembled. If desired, a visual or audible signal may also be generated. Thereafter the user removes the peelable sheet 14 to uncover the adhesive surface where after the device can be attached to a skin surface of the user, typically the abdomen. Infusion of drug is started by gripping and pulling away the actuation strip 21 as indicated by the arrow whereby the needle is inserted followed by automatic start of the infusion. The needle insertion mechanism may be supplied in a pre-stressed state and subsequently released by the actuation means or the needle insertion may be "energized" by the user. A "beep" signal confirms that the device is operating and drug is infused. The reservoir unit is preferably provided with signal means and detection means providing the user with an audible alarm signal in case of e.g. occlusion, pump failure or end of content.

After the device has been left in place for the recommended period of time for use of the needle unit (e.g. 48 hours)—or in case the reservoir runs empty or for other reasons—it is removed from the skin by gripping and pulling the retraction strip 22 which leads to retraction of the needle followed by automatic stop of drug infusion where after the strip which is attached to the adhesive patch is used to remove the device from the skin surface.

When the device has been removed the two units are disengaged by simultaneously depressing the two hook members 31 allowing the reservoir unit 5 to be pulled out of engagement with the needle unit 2 which can then be discarded. Thereafter the reservoir unit can be used again with fresh needle units until it has been emptied.

Figure 3:
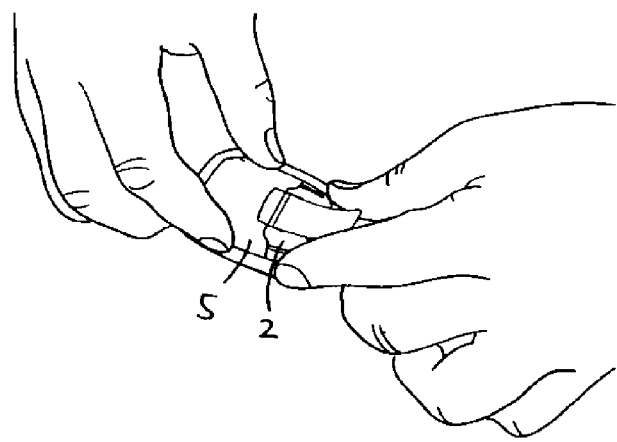
Figure 4:
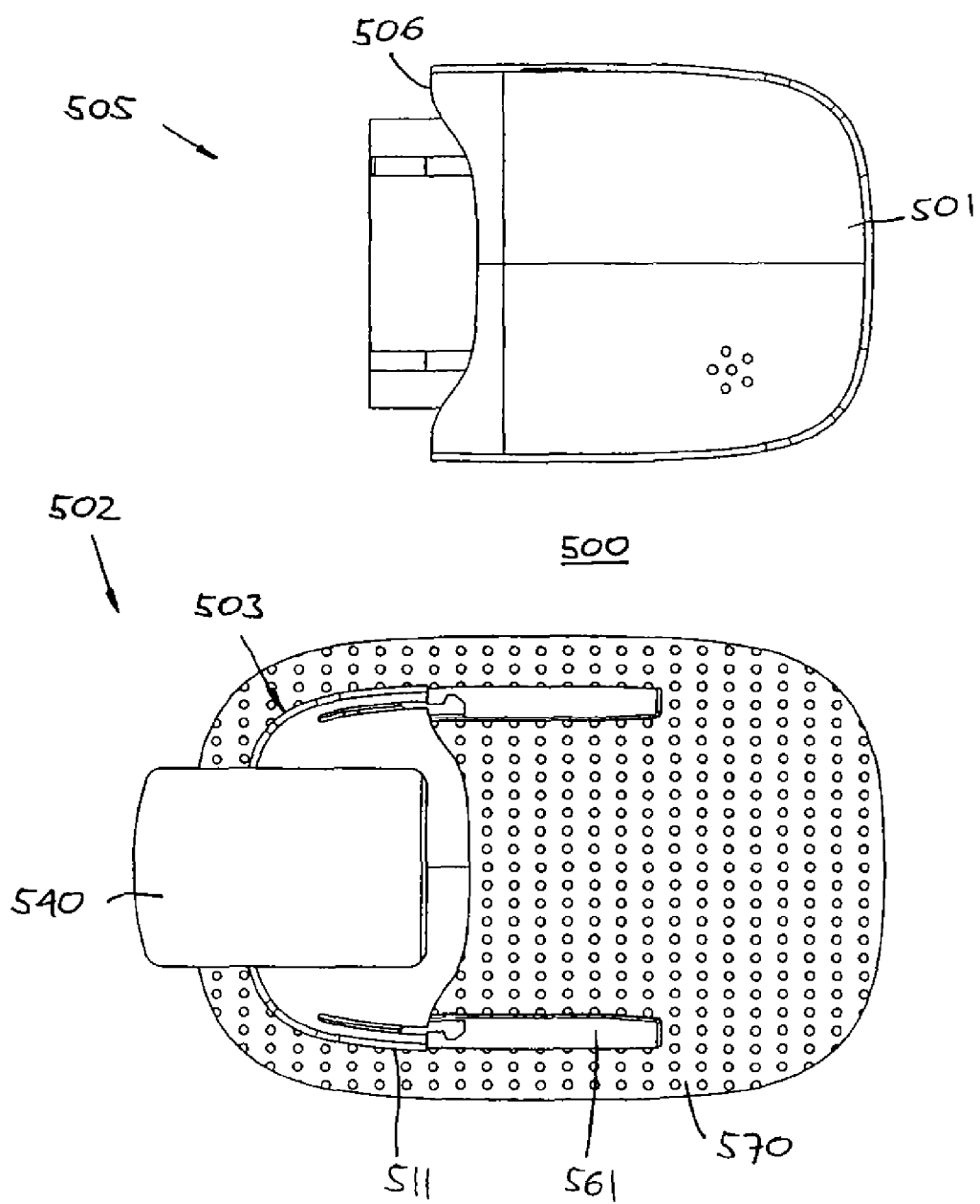
FIG. 4 shows in a non-assembled state a needle unit and a reservoir unit for a further embodiment of a drug delivery device.

FIG. 4 shows a further embodiment of medical device 500 substantially corresponding to the embodiment of FIG. 1, the device comprising a transcutaneous device unit 502 and a process unit 505, More specifically, the transcutaneous device unit comprises a flexible patch portion (in the shown embodiment formed by a perforated sheet member 570) comprising an upper surface and a lower surface, the lower surface being adapted for application to the skin of a subject, a first housing 503 comprising a first coupling with two male coupling elements 511, and a transcutaneous device arranged in the housing (see below). Two supporting ridge members 561 extend from the first housing and are attached to the upper surface of the sheet member. The supports serve as attachment supports for the first housing, however, they may also serve to control the distance between the lower surface or the process unit and the patch. When the second unit is configured to accommodate at least partially the support members, e.g. in corresponding cut-out portions or grooves 504 (see FIG. 12), the supports may also serve to laterally stabilize the connection between the two units. The process unit comprises a second housing 501 with a lower surface and a second coupling arranged at a peripheral portion of the second housing, and a process assembly, e.g. a pump assembly as will be described below. In the shown embodiment the process unit has a generally flat rectangular shape with a cut-off end portion defining the interface with the transcutaneous device unit and also comprising the coupling in the form of two female coupling elements 506 arranged at each side of the end portion. Corresponding to FIGS. 1-3, the first and second couplings can be connected to each other with the upper surface of the patch facing towards the lower surface of the second housing. Due to the peripheral arrangement of the second coupling the flexible patch portion facing towards the lower surface of the second housing is free to move relative thereto, the degree of freedom being determined by the flexibility of the patch and supports if so provided and, of course, the surface to which the transcutaneous device unit is mounted.

In the shown embodiment the patch portion has the same general shape as the combined device albeit somewhat larger. In alternative embodiments the patch may comprise openings or cut-out portions. For example, an area between the two support legs may be cut out allowing the underlying skin to better breath.

Figure 14:
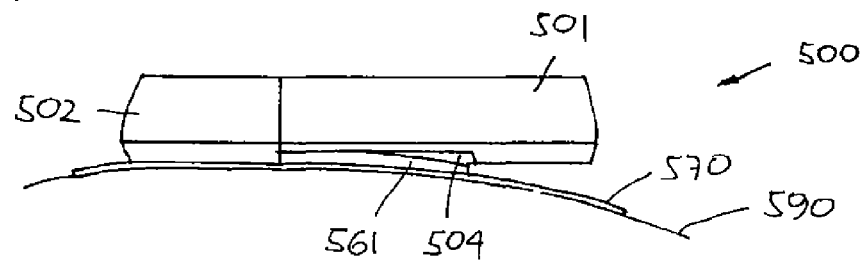
FIG. 14 shows a side view of a medical device mounted on a curved skin surface.
Figure 17:
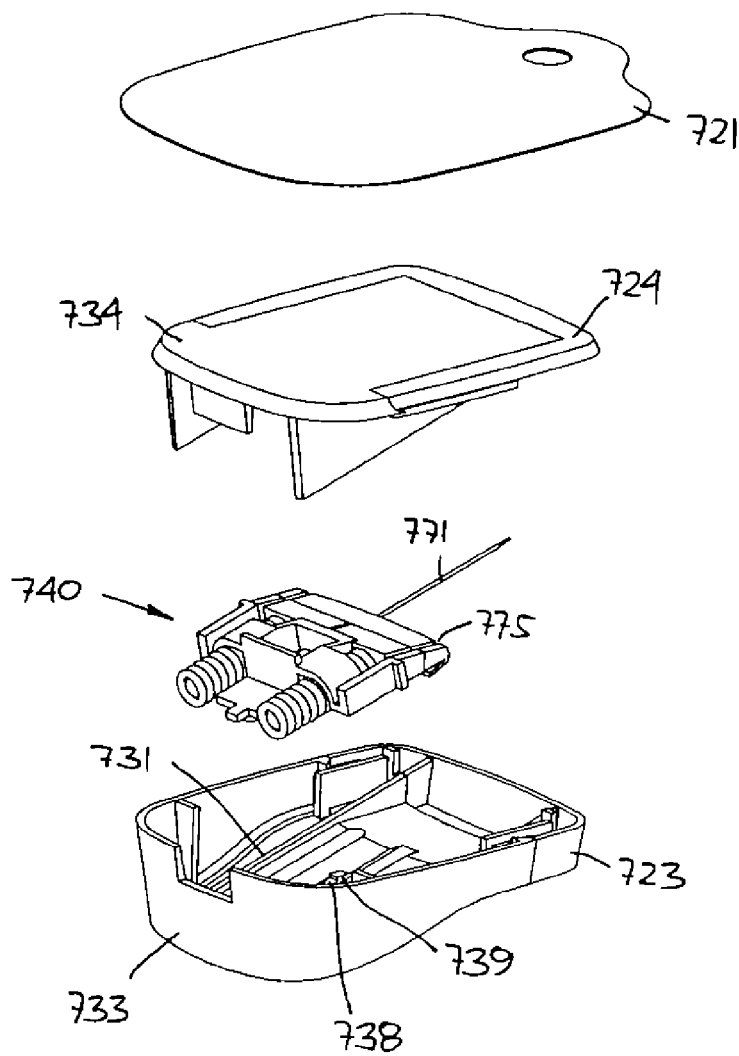
FIG. 17 shows the device of FIG. 16 from below.

FIG. 14 shows a side view of the assembled device 500 mounted on a curving skin surface 590. As appears, the flexible patch portion with its support members is allowed to follow the curvature of the skin, this creating a ventilation space between the process unit and the patch portion.

Figure 5:
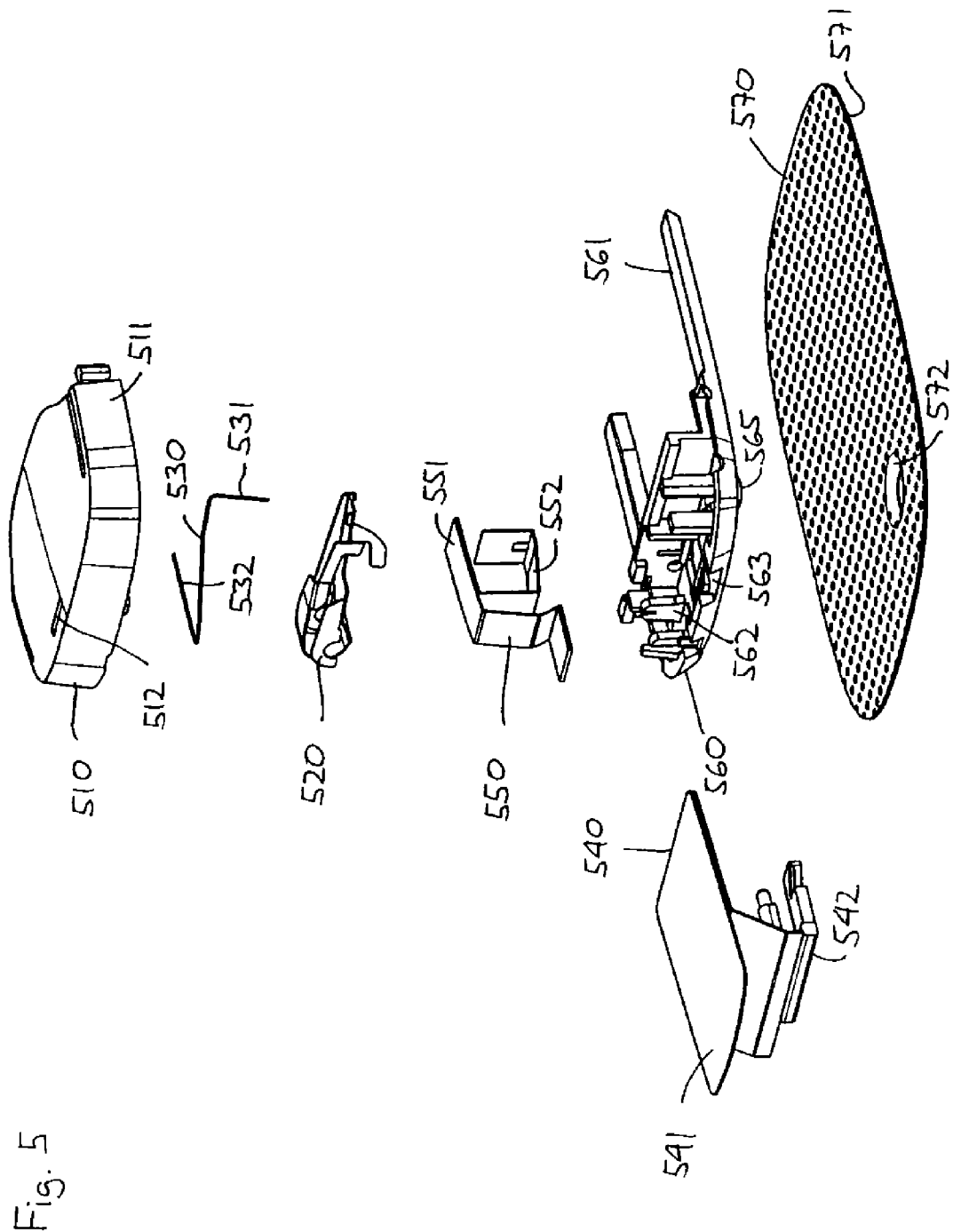
FIG. 5 shows an exploded view of the needle unit of FIG. 4.
Figure 6:
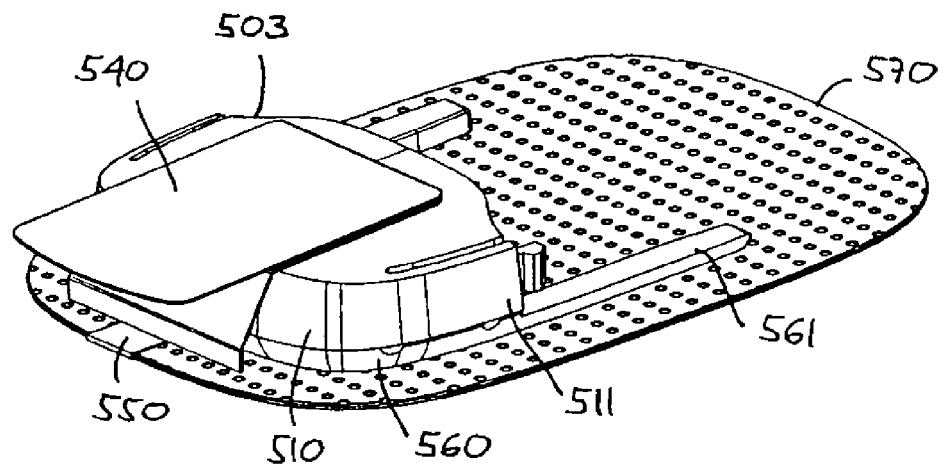
FIG. 6 shows a perspective view of the needle unit of FIG. 4 in a first state.

FIG. 5 shows an exploded perspective view of the needle unit comprising an upper housing portion 510, a needle carrier 520 and a thereto mounted infusion needle 530, an actuation member 540, a release member 550, a lower housing portion 560 and a sheet member 570 with a lower adhesive mounting surface 571. The actuation member comprises a user gripable portion 541 and a needle actuation portion 542, and the release member comprises a user gripable portion 551 and a needle retraction portion 552. In the assembled state as shown in FIG. 6, the upper and lower housing portions form a housing 503 in which the needle and the needle carrier is mounted, the actuation and release members being operatable connected to the needle carrier with the user gripable portions arranged outside the housing. The sheet member further comprises an opening 572 arranged in register with a lower protrusion 565 provided around the exit aperture for the transcutaneous device, just as the sheet is provided with a large number of small perforations to improve breathability through the sheet. The housing 503 is provided with user actuatable coupling means 511 allowing a reservoir unit to be attached to and released from the needle unit 505, the reservoir unit comprising corresponding mating coupling means 506 as well as a display 587. The display may indicate e.g. proper function of the unit, the amount of drug in the reservoir or different error conditions.

As seen is the user gripable portion 551 of the release member initially covered by a portion of the actuation member, this reducing the probability that the user erroneously uses the release member instead of the actuation member. Further, the actuation and release members (or portion thereof) may be colour coded to further assist the user to correctly use the device. For example, the actuation member may be green to indicate "start" whereas the release member may be red to indicate "stop".

Figure 7:
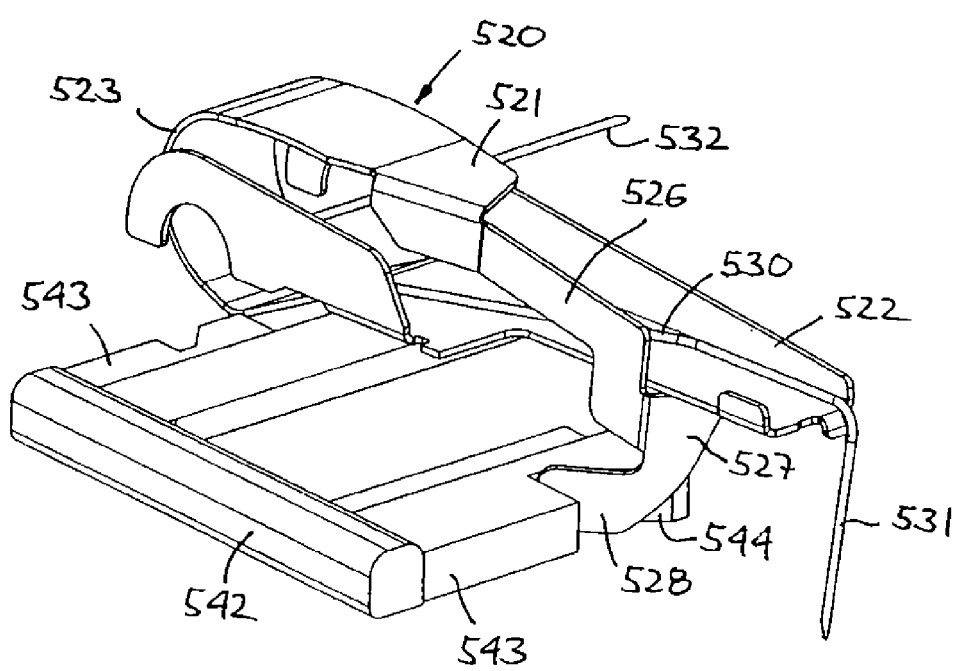
FIG. 7 shows a perspective view of the needle carrier of FIG. 5.

FIG. 7 shows in perspective the needle carrier 520 with the needle 530 and the needle actuation portion 542 of the actuation member 540. The needle actuation portion comprises two legs 543 allowing it to slide relative to the housing, the legs being arranged through respective openings 563 in the housing. The needle carrier is adapted to be connected to a hinge member 562 of the lower housing portion to thereby allow the needle carrier and thereby the needle to pivot corresponding to a pivoting axis defined by a hinge. In the shown embodiment is the needle carrier in the form a bent sheet metal member, the carrier comprising an upper arm 521 and a lower arm 522 connected to each other by a hinge portion 523 allowing the lower arm to pivot relative to the upper arm and corresponding to the pivoting axis. The lower arm forms a tray in which the hollow infusion needle 530 is mounted (e.g. by welding or adhesive), the needle having a distal pointed portion 531 adapted to penetrate the skin of the subject, the distal portion extending generally perpendicular to the mounting surface of the needle unit, and a proximal portion 532 arranged substantially corresponding to the pivoting axis and adapted to engage a fluid supply. Thus, when a portion of the upper arm is mounted in the housing, the lower arm can pivot between a first retracted position in which the distal portion of the needle is retracted within the housing, and a second extended position in which the distal portion projects relative to the mounting surface. In the shown embodiment the needle carrier provides the drive means for moving the lower arm between the two positions. This may as in the present embodiment be provided by the elastic properties of the sheet material per se corresponding to the hinge portion, or alternatively an additional spring may be provided between the two arms to thereby urge them apart. To lock the lower part in an energized, releasable first position, the upper arm is provided with a flexible release arm 526 comprising a catch 527 supporting and arresting the lower arm in its first downwardly biased position, as well as a release portion 528 engaging a ramp surface 544 of the needle actuation portion 542, the catch further comprising an inclined edge portion 529 adapted to engage the lower arm when the latter is moved from its extended to its retracted position as will be described in greater detail below.

Figure 8:
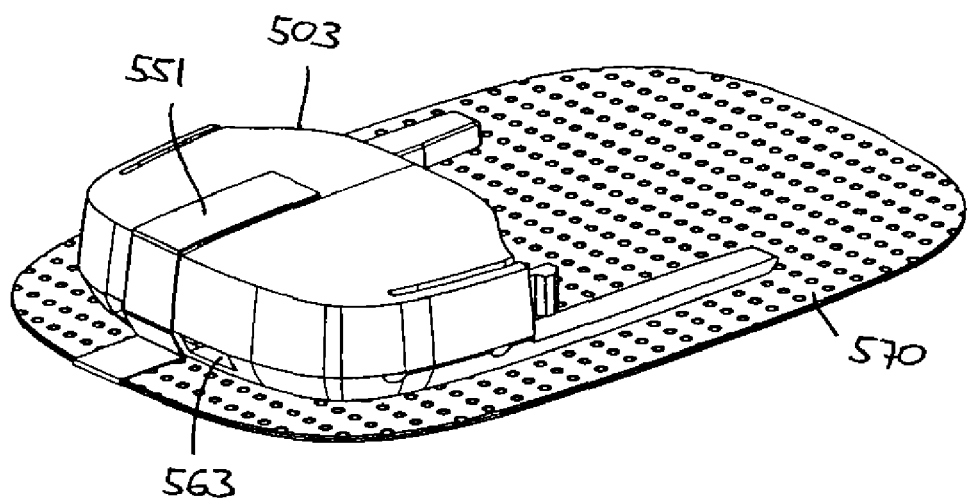
FIG. 8 shows a perspective view of the needle unit of FIG. 4 in a second state.

To actuate the needle the user grips the flexible strip forming the user gripable portion 541 (which preferably comprises adhesive portions to hold it in its shown folded initial position) and pulls the needle actuation portion 542 out of the housing, the actuation member 540 thereby fully disengaging the housing. More specifically, when the ramp surface 544 is moved it forces the latch 527 away from the lower arm to thereby release it, after which the release portion 528 disengages the ramp allowing the two legs to be pulled out of the housing. As seen in FIG. 8, when the actuation member is removed the user gripable portion 551 of the release member is exposed. As for the actuation member, the user gripable portion of the release member preferably comprises adhesive portions to hold it in its shown folded initial position.

Figure 9:
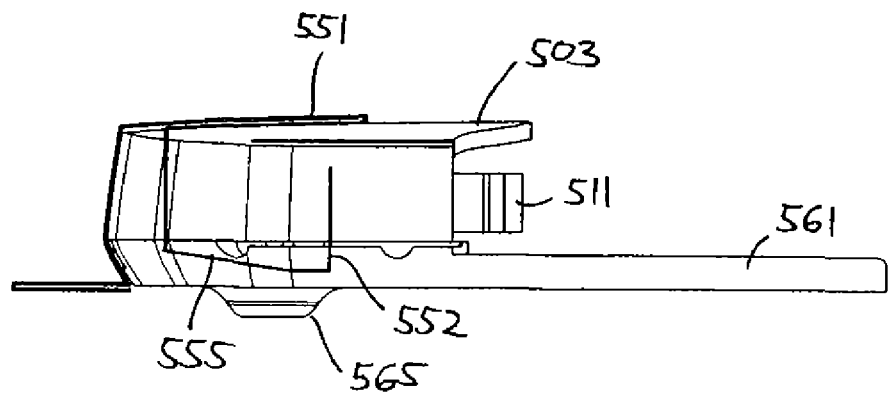
FIG. 9 shows a side view of the needle unit of FIG. 4.

In the shown embodiment the release member is in the form of a strip formed from a flexible material and having an inner and an outer end, the strip being threaded through an opening 512 in the housing, the strip thereby forming the user gripable portion 551 and the needle retraction portion 552, the inner end of the strip being attached to the housing and the outer end of the strip being attached to a peripheral portion of the sheet member 570 or, alternatively, a peripheral portion of the housing. In the projection shown in FIG. 9 the release member is shown in its initial position, the retraction portion forming a loop 555 arranged below the lower arm of the needle carrier, this position allowing the lower arm to be moved to its actuated position and thereby the needle to its extended position.

When the user decides to remove the needle unit from the skin, the user grips the user gripable portion 551, lifts it away from the housing and pulls it upwardly whereby the loop shortens thereby forcing the lower arm upwardly, this position corresponding to an intermediate release state. By this action the lower arm engages the inclined edge portion 529 of the catch 527 thereby forcing it outwardly until it snaps back under the lower arm corresponding to the position shown in FIG. 7. As the actuation member 540 has been removed from the needle unit, the needle carrier is irreversibly locked in its retracted position. When the user further pulls in the release member, the peripheral portion of the sheet member to which the release member is attached will be lifted off the skin, whereby the needle unit with its attached reservoir unit can be removed from the skin, this as described above.

Advantageously, the actuation and release members may be formed and arranged to communicate with the reservoir unit (not shown). For example, one of the legs of the actuation member may in its initial position protrude through the housing to thereby engage a corresponding contact on the reservoir unit, this indicating to the reservoir unit that the needle unit has been attached, whereas removal of the actuation member will indicate that the needle has been inserted and thus that drug infusion can be started. Correspondingly, actuation of the release member can be used to stop the pump.

Figure 10:
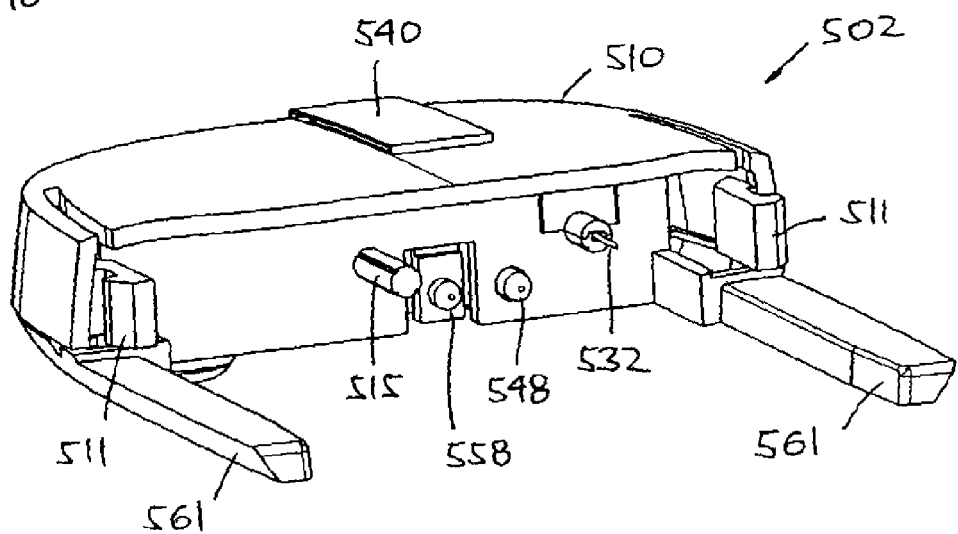
FIG. 10 shows a further perspective view of the needle unit of FIG. 4.

In FIG. 10 the side of the needle unit 502 which connects to the reservoir unit is shown. In addition to the two ridge members 561 and the user actuatable coupling means 511 the needle unit comprises further structures which connects to and/or engages the reservoir unit to provide a functional interface with the reservoir unit. More specifically, the needle unit comprises a fluid inlet provided by the pointed proximal portion 532 of the needle projecting from the needle unit and adapted to engage a fluid outlet of the reservoir unit, an actuator 515 projecting from the needle unit and adapted to engage and actuate a fluid connector in the reservoir unit (see below), and first and second contact actuators 548, 558 adapted to engage corresponding contacts on the reservoir unit. The first contact actuator is provided by the distal end of one of the legs 543 of the needle actuator projecting through an opening in the housing, and the second contact actuator is provided by a hinged portion of the housing connected to the needle retraction portion 552 of the release member 550. When the needle unit is first connected to the reservoir unit both contact actuators will protrude from the housing and engage the corresponding contacts on the reservoir unit thereby indicating that that a needle unit has been connected. When the needle is actuated the first contact actuator will be withdrawn and thereby disengage the corresponding contact on the reservoir unit to start pump actuation. When the needle is retracted the second contact actuator will pivot and disengage the corresponding contact on the reservoir unit to stop pump actuation.

Figure 11:
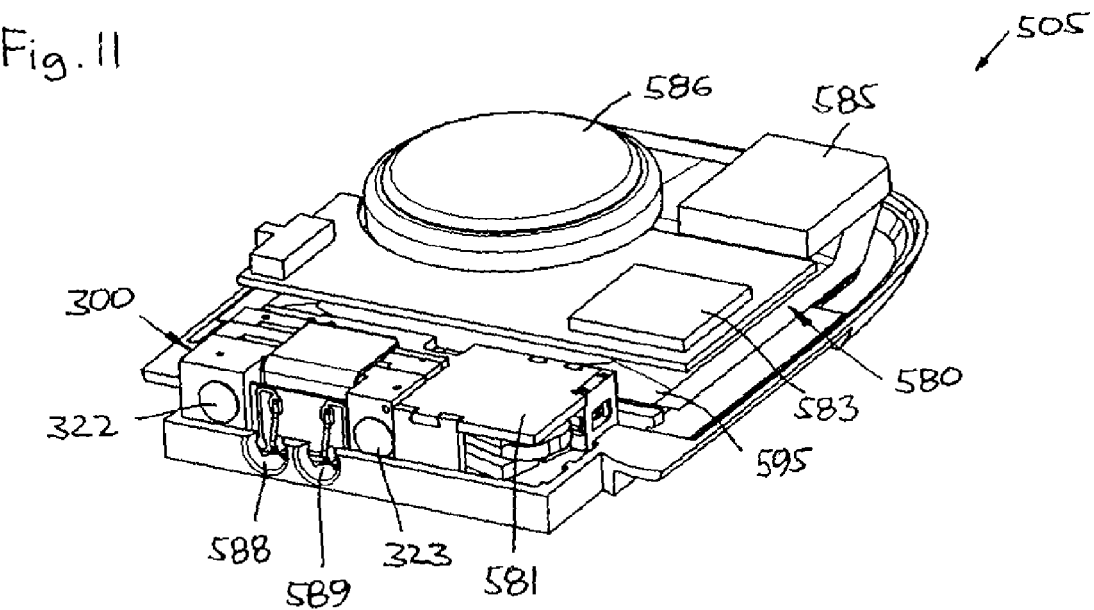
FIG. 11 shows perspective view of the interior of the reservoir unit of FIG. 4.

FIG. 11 shows the reservoir unit with an upper portion of the housing removed. The reservoir unit comprises a reservoir 595 and an expelling assembly comprising a pump assembly 300 and control and actuation means 580, 581 therefore. The pump assembly comprises an outlet 322 for connection to a transcutaneous access device (e.g. the needle 530) and an opening 323 allowing an internal fluid connector to be actuated, see below. The reservoir 560 is in the form of prefilled, flexible and collapsible pouch comprising a needle-penetratable septum adapted to be arranged in fluid communication with the pump assembly, see below. The shown pump assembly is a mechanically actuated membrane pump, however, the reservoir and expelling means may be of any suitable configuration.

The control and actuation means comprises a pump actuating member in the form of a coil actuator 581 arranged to actuate a piston of the membrane pump, a PCB or flex-print to which are connected a microprocessor 583 for controlling, among other, the pump actuation, contacts 588, 589 cooperating with the contact actuators on the needle unit, signal generating means 585 for generating an audible and/or tactile signal, a display (not shown) and an energy source 586. The contacts are preferably protected by membranes which may be formed by flexible portions of the housing.

The membrane pump may comprise a piston-actuated pump membrane with flow-controlled inlet- and outlet-valves. The pump has a general layered construction comprising a number of body members between which are interposed flexible membrane layers, whereby a pump chamber, inlet and outlet valves, and one or more safety valves can be formed. The pump further comprises a fluid connector in the form of hollow connection needle slidably positioned within the pump behind the connection opening 323, this allowing the pump to be connected with reservoir. For a more detailed description of such a membrane pump reference is made to applicants co-pending application PCT/EP2006/060277, which is hereby incorporated by reference.

Figure 12:
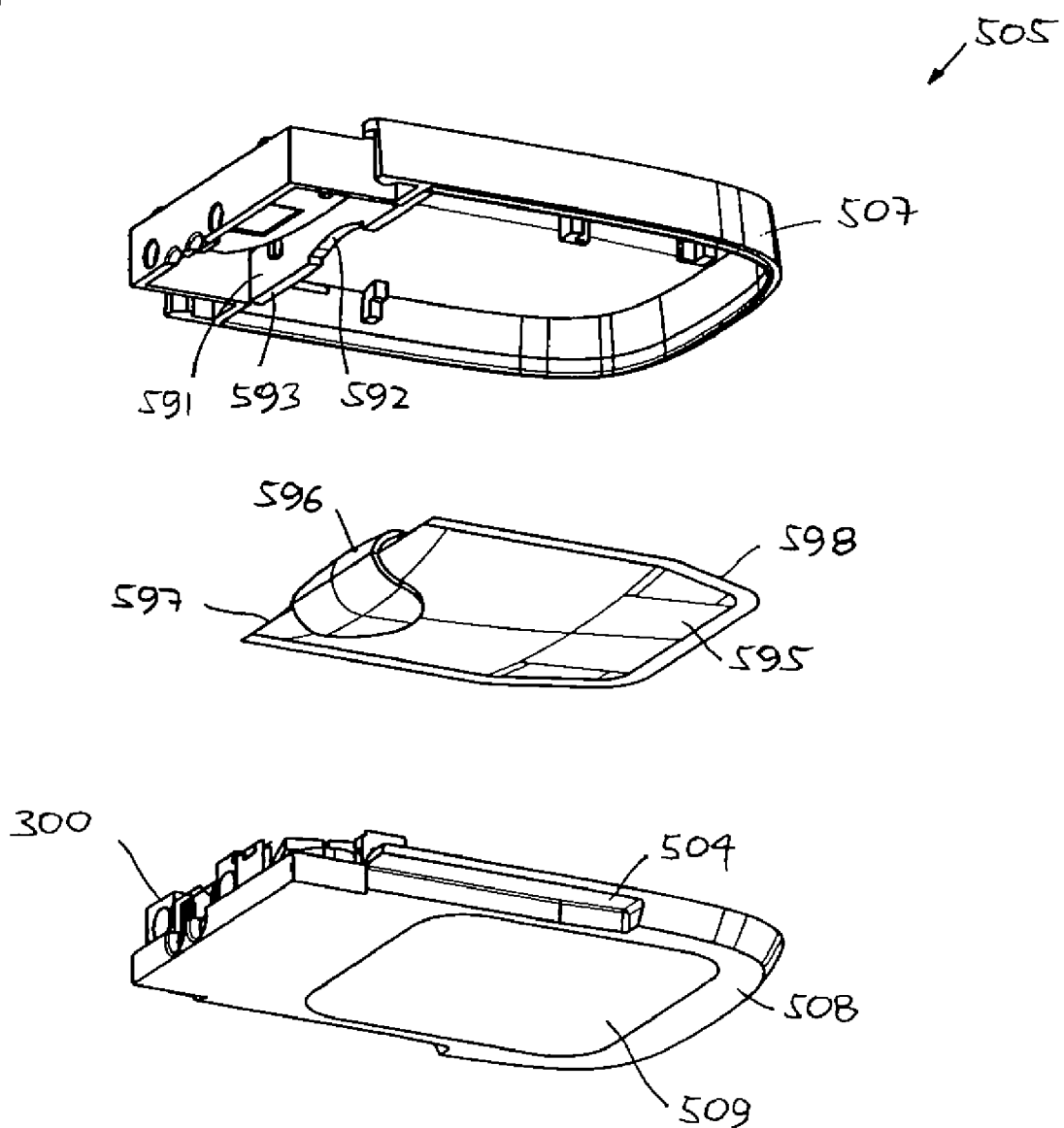
FIG. 12 shows an exploded view of a further reservoir unit.

In FIG. 12 an exploded view of the reservoir unit 505 of FIG. 4 is shown, the unit comprising an upper housing member 507, a lower housing member 508 with a transparent area 509 and grooves 504 to receive the ridge members 561 extending from the needle unit, a flexible reservoir 595 with a rounded edge portion 597 on which a septum member 596 is mounted, a pump assembly 300 with actuator and a circuit board (not shown) arranged above the reservoir and comprising electronic components for controlling actuation of the pump. The upper and lower housing members comprise reservoir mounting means in the form of opposed upper and lower ridge portions 591 (the lower not seen) adapted to engage and mount the reservoir in the housing. Each ridge portion comprises a central cut-out portion 592 adapted to engage the septum member on its opposed surfaces when the housing members are assemble thereby locking the reservoir in place within the housing. The degree of locking will be determined by the pressure exerted on the septum member, the elastic properties of the septum member and the friction between the ridge and the septum member. On each side of the cut-out portion the ridge portions comprise a straight portion 593 which may aid in mounting the reservoir in the housing. The straight portions may engage the initially prefilled reservoir to help lock it in place, however, as the reservoir is emptied and flattens this grip may lessen. In contrast, the engagement with the septum is adapted to properly hold the reservoir in place as the reservoir is emptied. The straight portions may also be adapted to pinch and fully flatten the reservoir thus serving as an additional mounting means. Additional mounting means (not shown) may engage and grip the reservoir at other locations, e.g. along the welded edges 598.

In the above described embodiments, the transcutaneous device has been in the form of a unitary needle device (e.g. an infusion needle as shown or a needle sensor (not shown), however, the transcutaneous device may also be in the form of a cannula or a sensor in combination with an insertion needle which is withdrawn after insertion thereof. For example, the first needle portion may be in the form of a (relatively soft) infusion cannula (e.g. a Teflon® cannula) and a there through arranged removable insertion needle. This type of cannula needle arrangement is well known from so-called infusion sets, such infusion sets typically being used to provide an infusion site in combination with (durable) infusion pumps.

Figure 13A:
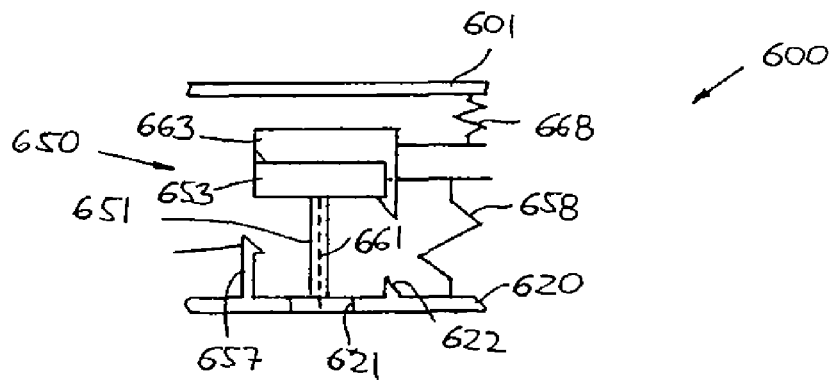
FIGS. 13A and 13B show in a schematic representation a transcutaneous device in the form of a cannula and insertion needle combination.
Figure 13B:
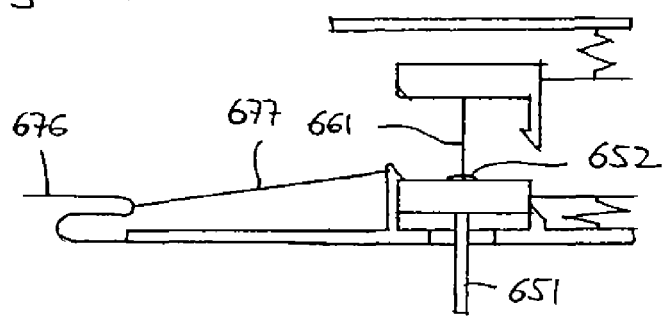

Thus, FIGS. 13A and 13B show in a schematic representation how a cannula and insertion needle combination can be arranged within a housing 601 of in a given medical device 600 (partly shown), e.g. an infusion device or an infusion set. More specifically, the medical device comprises a transcutaneous assembly 650 comprising a combination of a relatively soft cannula 651 (which e.g. may be of the soft "Teflon®" type) carried by a lower member 653 and a pointed insertion needle 661 (e.g. made from medical grade stainless steel) slidably arranged within the cannula and carried by an upper member 663, both members being mounted to allow axial displacement of the cannula respectively the insertion needle. The cannula comprises a proximal inlet (not shown) allowing it to be or to be arranged in fluid communication with a fluid source. The medical device further comprises a base plate 620 with an opening 621 for the cannula as well as a release member 622. The lower member comprises an elastomeric seal 652 through which the insertion needle is arranged. The cannula and the insertion needle may be straight or curved dependent upon how the two members are mounted in the device, e.g. arcuate corresponding to a pivoting axis or straight corresponding to linear movement as illustrated. The upper member comprises a coupling member 667 locking the members together in an initial position with distal end of the insertion needle extending from the distal opening of the cannula as shown in FIG. 13A, and the base plate comprises coupling member 657 for locking the lower member in an extended position with distal end of the cannula extending through the opening in the base plate (see FIG. 13B). Between the housing of the device and the upper member a first spring 668 is arranged biasing the upper member upwards. Correspondingly, the device also comprises a second spring 658 biasing the lower member upwardly. The medical device further comprises a gripping tab 676 and a pulling member 677 corresponding to the embodiment shown in FIG. 1.

In a situation of use the assembly is moved downwardly, either manually or by a releasable insertion aid, e.g. a spring loaded member acting through an opening in the housing (not shown) whereby the cannula with the projecting insertion needle is inserted through the skin of a subject. In this position the lower member engages the coupling member 657 to thereby lock the cannula in its extended position, just as the coupling member 667 is released by the release member 622 thereby allowing the upper member to return to its initial position by means of the first spring.

When the user intends to remove the delivery device from the skin surface, the user grips the gripping portion of the tab and pulls it in a first direction substantially in parallel with the skin surface, by which action the flexible strip 677 releases the coupling member 657 from the lower member whereby the lower member and thereby the cannula is retracted by means of the second spring. When the cannula has been withdrawn from the skin, the user uses the now unfolded tab to pull off the entire delivery device from the skin surface, for example by pulling the tab in a direction away from the skin surface.

With reference to FIGS. 15-18 a medical device 700 will be described comprising a cannula and an insertion needle (in the following also "needle" for short). The cannula may be in the form of what is traditionally referred to as a "soft catheter" or a "Teflon® catheter". The device comprises two portions, a patch unit 710 comprising a housing mounted on a patch of flexible sheet material, and an inserter unit 720 removeably coupled to the patch housing. The inserter housing initially comprises the entire insertion mechanism including the cannula.

When actuated the cannula becomes attached to the patch housing where after the inserter housing with the remaining inserter mechanism can be detached and discarded.

More specifically, the patch unit comprises a flexible sheet 721 with a lower adhesive surface and an opening 722 for the cannula, a patch housing with top 723 and base 724 portions, the base portion being attached to the upper surface of the sheet. The patch housing comprises an opening 725 for the cannula arranged just above the opening in the sheet, as well as a coupling in the form of two flexible arms 726 allowing the inserter to be attached.

The inserter unit comprises an inserter housing with top 733 and base 734 portions, the base portion comprising two walls 735 with upper inclined edges serving as a ramp 736 for an inserter assembly 740. The inserter assembly comprises an inserter 750, a needle holder 760 comprising a needle 761 protruding there from, a cannula holder 770 with a cannula 771 protruding there from, the cannula comprising a proximal needle penetratable septum, two springs 751 mounted on respective spring guides 752 on the inserter, and a release and retraction strip 780 (see FIG. 18A). The strip comprises a proximal end projecting from the housing and a distal end attached to the needle holder, the strip forming a loop portion attached to the inserter. The inserter and the cannula holder are each provided with pairs of grooves 755, 775 allowing the inserter and the cannula to slide on the ramp. The inserter comprises an opening 753, an inclined ramp member 754 and a locking projection 757 adapted to engage a corresponding opening 737 in the housing. The needle holder comprises a flexible release arm 763 with an upwardly protruding catch 762, and the cannula holder comprises a pair of coupling elements 772 for engagement with the patch housing. In an initial assembled state (see FIG. 17) the cannula holder is arranged in front of the inserter and the needle holder is arranged below the inserter with the needle positioned through the septum and within the cannula and projecting there from, and with the catch 762 protruding through the opening 753. As an example, the cannula may be a soft catheter with an OD of 0.7 mm and an ID of 0.4 mm and the needle may have an OD of 0.4 mm (G27). The inner surface of the inserter housing comprises a ramp 738 and a hold 739 adapted to engage the inserter assembly as described below. In a fully assembled initial state the inserter assembly is locked in place by the locking projections 757 engaging the opening 737 in the inserter housing, the springs being arranged in a compressed state between the inserter and the inserter housing. Upper guides 731 in the inserter housing secures that the inserter assembly can move only along the inclined ramp.

Next, with reference to FIGS. 18A-18F operation of a medical device of the above-outlined construction for insertion of a soft catheter will be described. The user first removes a protective sheet covering the adhesive surface of the patch and arranges the patch on a suitable skin portion of a subject, e.g. the abdomen. In the start position (see FIG. 18A) the soft catheter holder with a soft catheter is placed in front of the inserter. The needle holder is connected to the inserter, which is loaded with springs (see FIG. 15), all integrated in the inserter housing. The inserter needle is arranged inside the soft catheter with its pointed needle tip e.g. 2 mm in front of the soft catheter. Next the user pulls the strip which releases the inserter from the housing, this allowing the inserter assembly with soft catheter and needle holder to start move forwards pushed by the springs. As appears, by this action the strip is released from the needle holder. By the initial travel of the inserter assembly the inserter needle with soft catheter penetrates dermis 2-4 mm. During this movement the catch of the release arm on the needle-holder engages the ramp placed on the inserter-housing (see FIG. 18B). The ramp depresses the release arm in relation to its engagement with the inserter, and finally arrests the release arm as it engages the hold at the end of the ramp, this temporary halting movement of the needle holder. After needle movement has come to a halt, the inserter and the soft catheter holder continue forward movement driven by the springs, thereby moving the soft catheter ahead of the needle an into sub-cutis. The needle holder is stopped until the soft catheter tip is e.g. 1-5 mm in front of needle tip. During this movement the release arm on the needle holder is stopped by the hold in the housing, however, at the same time the flexible arm is engaged by the ramp member on the inserter. This ramp depresses the release arm until it is lifted free of the hold where after it again engages the inserter (see FIG. 18C). After the needle holder has re-engaged the inserter, the needle now follows the soft catheters movement through sub-cutis to a final position, and the needle can therefore act as guide for the soft catheter, with the tip of the needle e.g. 1-5 mm behind the tip of the soft catheter. When the cannula reaches its final fully extended position the soft catheter holder is positioned in the patch-housing where it is locked in place (see FIG. 18D). As appears, the above-described actions all take place automatically driven by the springs and in a very short time, this providing minimum discomfort to the subject.

At this point the soft catheter has been placed at the desired place and what remains is for the user to withdraw the needle and remove the remaining inserter assembly and housing. In the shown embodiment the inserter is locked in place in its foremost position. The needle holder is released from the inserter and the needle is retracted by the user pulling the strip attached to the needle holder until the needle has been locked in its fully retracted position with the distal pointed end arranged within the inserter housing (see FIG. 18E). In the shown embodiment the inserter serves to surround and protect the pointed end of the needle. Finally the user detaches the inserter housing from the patch unit which can then be disposed off (see FIG. 18F). The cannula is now ready to be connected to a fluid source, e.g. a reservoir unit as shown in FIG. 1 and of the same principal configuration as described with reference to FIGS. 11 and 12. Indeed, the interface of the pump assembly 300 will have to be modified in order to connect to the proximal septum of the soft catheter or cannula instead of a pointed needle end, i.e. the pump assembly will be provided with a pointed hollow needle establishing a fluid communication between the pump assembly and the inserted cannula.

With reference to FIGS. 15-18 an embodiment comprising a separate cannula inserter has been described, however, a corresponding mechanism may also be incorporated in a unitary patch unit. Such a design would indeed result in a larger patch housing, however, the user would not have to detach and discard the inserter. For such a design the needle may be hollow and comprise a proximal end, with the distal end of the needle being in sealed fluid communication with the interior of the cannula when the needle has been arranged in its retracted position. By this arrangement a fluid communication can be provided between the proximal end of the needle and the cannula, this allowing the fluid communication to be established between the patch unit and the reservoir unit corresponding to the connection between the units in the FIGS. 5-12 embodiment. In this case a delivery device would supply drug to the cannula via the hollow needle.

With reference to FIGS. 19-21 a further integrated concept will be disclosed. The concept consists of an introducer needle surrounding a cannula, e.g. a soft catheter. The 1-2 mm cutis or derma is penetrated by the needle and only the soft catheter is inserted into sub-cutis. Once the soft catheter is fully inserted, the needle is retracted. Since the needle is placed on the outside of the soft catheter, the soft catheter can be made in a smaller diameter compared to a concept in which the needle is arranged inside the needle and trauma in subcutis is thereby minimized, however, the larger diameter needle may cause larger trauma in the derma just as the cannula may be more susceptible to kinking and there may be less control when positioning the soft catheter in the subcutis. Also clotting during use may be more likely. These issues have to be considered when deciding on a specific concept and the specific design parameters for such a concept.

Turning to an exemplary embodiment, the medical device is in the form of a unitary patch unit 800 comprising a housing mounted on a patch of flexible sheet material, the inserter housing comprising the entire insertion mechanism including the cannula.

More specifically, the patch unit comprises a flexible sheet 821 with a lower adhesive surface and an opening 822 for the cannula (in this embodiment a flexible soft catheter), a patch housing with top 823 and base 824 portions (823' indicates a top portion shown upside down), with the base portion being attached to the upper surface of the sheet, wherein the top portion comprises a 45 degrees guide 825 for the cannula holder (see below). The patch housing comprises an opening for the cannula and needle arranged just above the opening in the sheet, as well as a coupling in the form of two flexible arms 826 allowing a delivery device to be attached. The base portion comprises two walls 835 with upper inclined edges serving as a ramp 836 for an inserter assembly 840. The inserter assembly comprises an inserter 850 with an attached needle 861 and a cannula holder 870 attached to a cannula 871 and adapted for moving the cannula relative to the inserter and thereby the needle (see FIGS. 20A and 20B). The inserter is provided with pairs of grooves allowing the inserter to slide on the ramp. The insertion mechanism further comprises a user-releasable spring (not shown) for moving the inserter and a strip (not shown) for moving the cannula holder relative to the inserter. As an example, the soft catheter may have an OD of 0.4 mm and an ID of 0.1 mm and the needle may have an OD of 0.7 mm and an ID 0.4 mm (G22).

To save space in the patch housing, the soft catheter introducing mechanism is placed perpendicular in respect of the direction of introduction. The soft catheter 871 is placed in a groove 855 in the inserter that guides the soft catheter, the groove having a 90 degrees bend to change the direction of the soft catheter during the introduction. As appears from FIGS. 20A and 20B when the catheter holder 870 is moved across the inserter the soft catheter is extended in a perpendicular direction.

Next, with reference to FIGS. 21A-21D operation of a medical device of the above-outlined construction for insertion of a soft catheter will be described. The user first removes a protective sheet covering the adhesive surface of the patch and arranges the patch on a suitable skin portion of a subject, e.g. the abdomen. In the start position (see FIG. 21A) the inserter is arranged in its retracted position and the cannula holder is arranged in its initial position. When the inserter is released (e.g. by pulling a strip to release a spring) the introducer needle with the soft catheter inside penetrates dermis e.g. 2-4 mm (see FIG. 21B). By continuous pulling the strip the user starts the introducing of the soft catheter into sub-cutis by pulling the soft catheter holder across the inserter until the soft catheter is fully introduced (see FIG. 21C). After the soft catheter is fully introduced the user continues the pulling of the strip and pulls the soft catheter holder further across the inserter, however, as the soft catheter holder has reached the 45 degrees ramp, the inserter is forced backwards with the same speed as the soft catheter is moved forward, the result is that the soft catheter stays in its final position and the introducer needle on the inserter is removed and disappears into the patch housing (see FIG. 21D).

As the proximal end of the soft catheter is stationary, it may be provided with a pointed hollow needle which would allow a reservoir unit basically as shown in FIGS. 11 and 12 to be connected thereto.

Figure 21A:
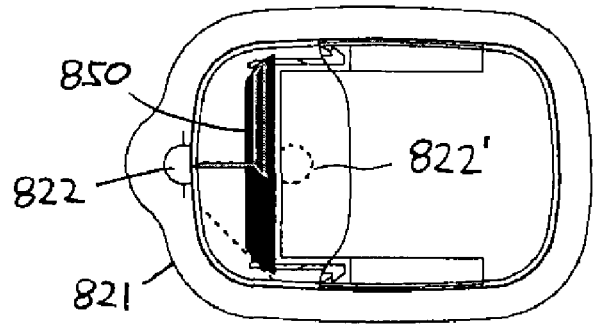
FIGS. 21A-21D show different states of use of the device of FIG. 19.
Figure 21B:
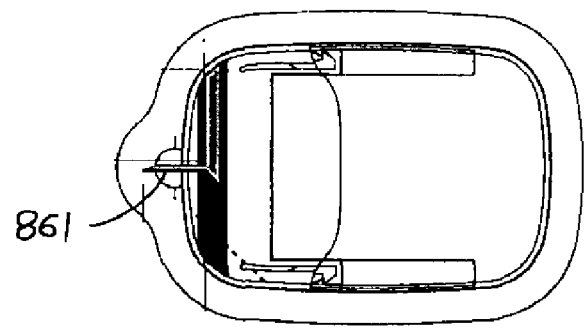
Figure 21C:
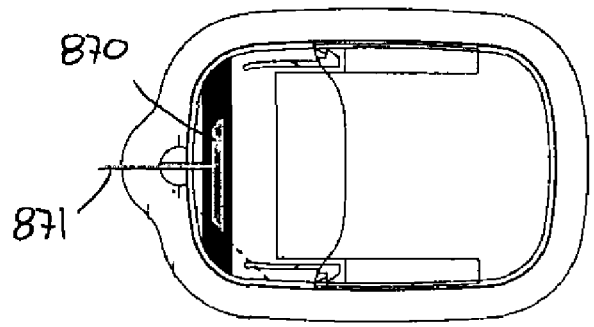
Figure 21D:
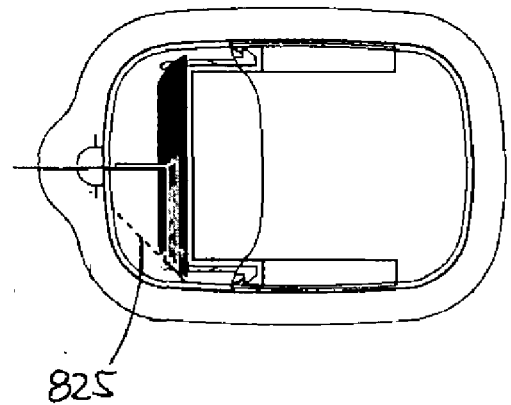
Figure 22:
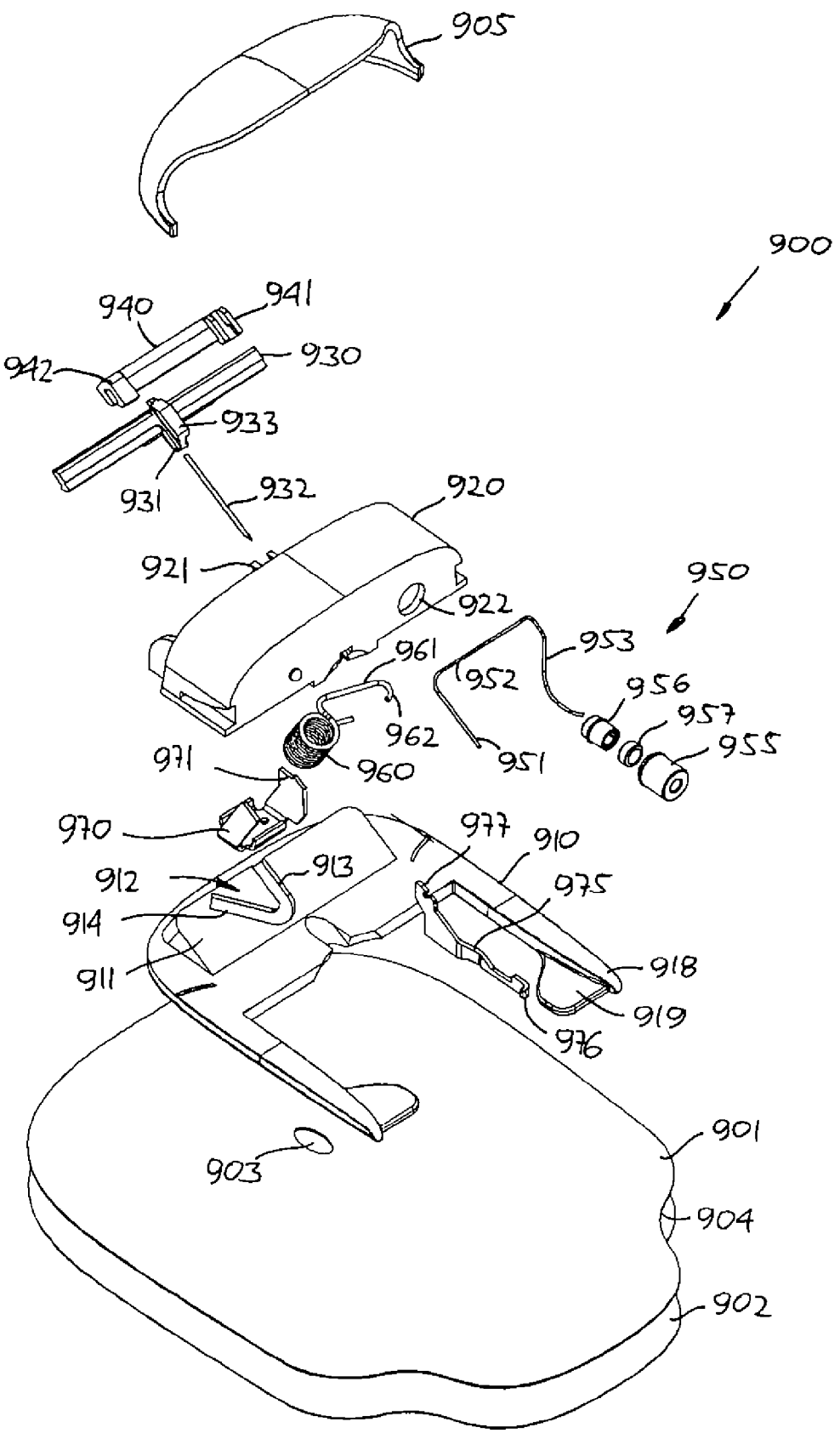
FIG. 22 shows in an exploded view a schematic representation of a transcutaneous device unit.

FIG. 22 shows in an upper exploded view a drawing of a schematic representation of a transcutaneous device unit (here a cannula unit) comprising a mechanism for inserting a soft cannula. The mechanism is similar to the mechanism described with reference to FIGS. 19-21. More specifically, the unit comprises a bottom part 910 onto which is mounted a chassis part 920 thereby creating an interior in which the different parts of the mechanism are arranged. In addition to the functional portions of the bottom and chassis part the mechanism comprises a needle holder 930 with a needle mount 931 to which a needle 932 is mounted, a cannula holder 940 comprising first and second gripping portions 941, 942 adapted to engage the needle holder, and a hollow cannula assembly comprising a soft, flexible cannula with a distal portion 951, an intermediate portion 952, and a proximal portion 953, the cannula assembly further comprising a tubular housing member 955 adapted to engage an opening 922 in the chassis portion, an elastomeric tubular member 956 in which the proximal end of the cannula is mounted, and a needle pierceable elastomeric septum, the tubular member and the septum being arranged in the housing member thereby providing a fluid inlet port for the hollow cannula. The mechanism further comprises a coil-formed torsion spring 960 comprising an actuator arm 961 with a curved distal end 962, the spring being arranged in a spring holder 970 comprising a catch 971 allowing the spring to be mounted in a pre-tensioned state. A release member 975 is provided comprising an outer end portion 976 adapted to engage e.g. a pump unit when the latter is mounted, and an inner end portion 977 adapted to engage and release the actuator arm from the spring holder. The bottom part comprises an inclined surface 911 with a guide 912 comprising a first guide groove 913 arranged corresponding to a longitudinal axis of the unit, and a second guide groove 914 arranged at an angle of 45 degrees relative to the first guide groove.

In the assembled state the cannula holder is mounted on the needle holder with the gripping portions 941, 942 arranged on each side of the needle mount 931, this allowing the cannula holder to slide along the length of the needle holder, the two holders thereby forming an inserter. In an initial state the distal portion of the cannula is positioned in the needle and the intermediate portion is positioned in a channel formed between the needle holder and the cannula holder, the cannula being mounted to the cannula holder by means of a flexible member on the first gripping portion.

Figure 24:
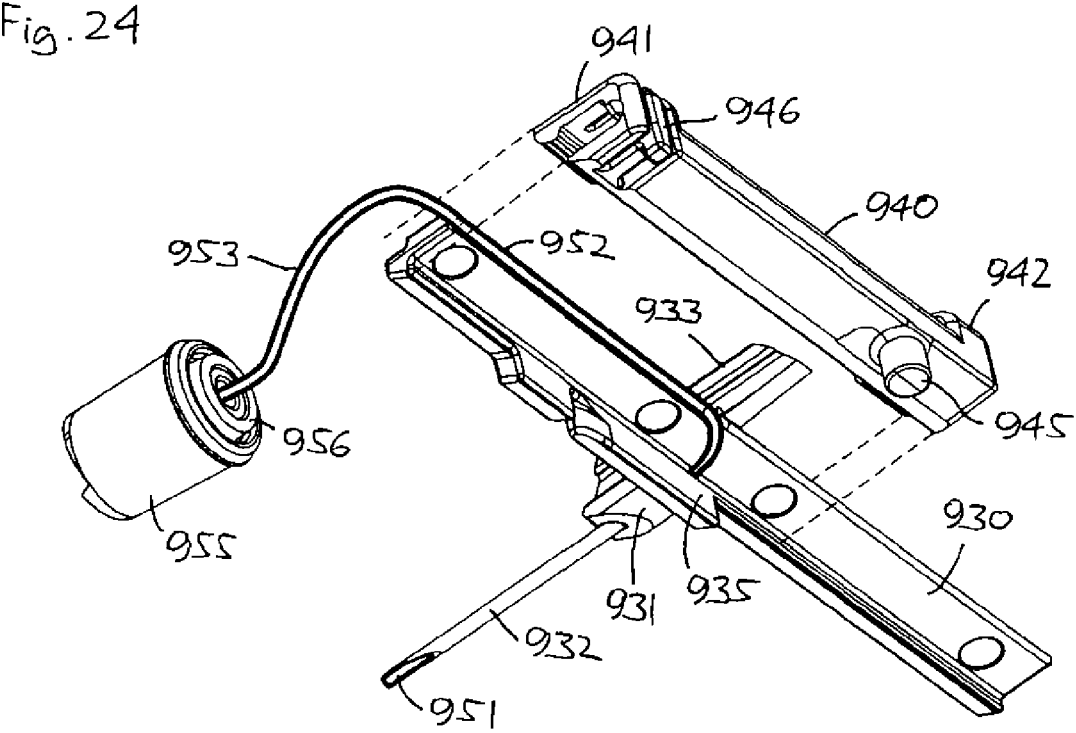
FIG. 24 shows an exploded view of an inserter.

In the assembled state the needle holder with the cannula holder mounted is arranged on the inclined surface and is allowed to slide up and down, with the guide grooves adapted to engage a guide member arranged on the lower surface of the cannula holder (not shown, see e.g. FIG. 24). To control movement of the needle holder the needle mount comprises a guide portion 933 with two opposed grooves adapted to engage a corresponding guide member 921 arranged on an interior surface of the chassis part. As appears, in the shown schematic drawing the inclined surface 911 is shown without cut-out portions allowing the release member 975 and the spring holder 970 to be mounted (see below).

The bottom part 910 further comprises two opposed leg portions 918 each with a lobe 919, the lobes providing attachment points when the bottom part is mounted to a flexible sheet or foil member 901 comprising an adhesive lower mounting surface 904 allowing the transcutaneous unit to be mounted on a skin surface of a subject. The sheet member comprises a central opening 903 through which the needle and cannula is introduced, as well as a release liner 902. A cover portion 905 serves to close the interior thereby forming a substantially closed housing.

With reference to FIGS. 23A-23D the mechanism described with reference to FIG. 22 is shown in a partly assembled state, the chassis part and the proximal portion of the cannula not being shown. The assembled embodiment differs slightly from the above-described embodiment, however, as the differences are small the same reference numerals are used.

The assembled embodiment primarily differs from the FIG. 23 embodiment in that the inclined surface 911 has been replaced with a number of wall members, the upper surfaces of these wall members in combination providing an inclined "surface" on which the needle holder is arranged, this allowing the spring 960 and release member 975 to be shown functionally correctly arranged.

Figure 23A:
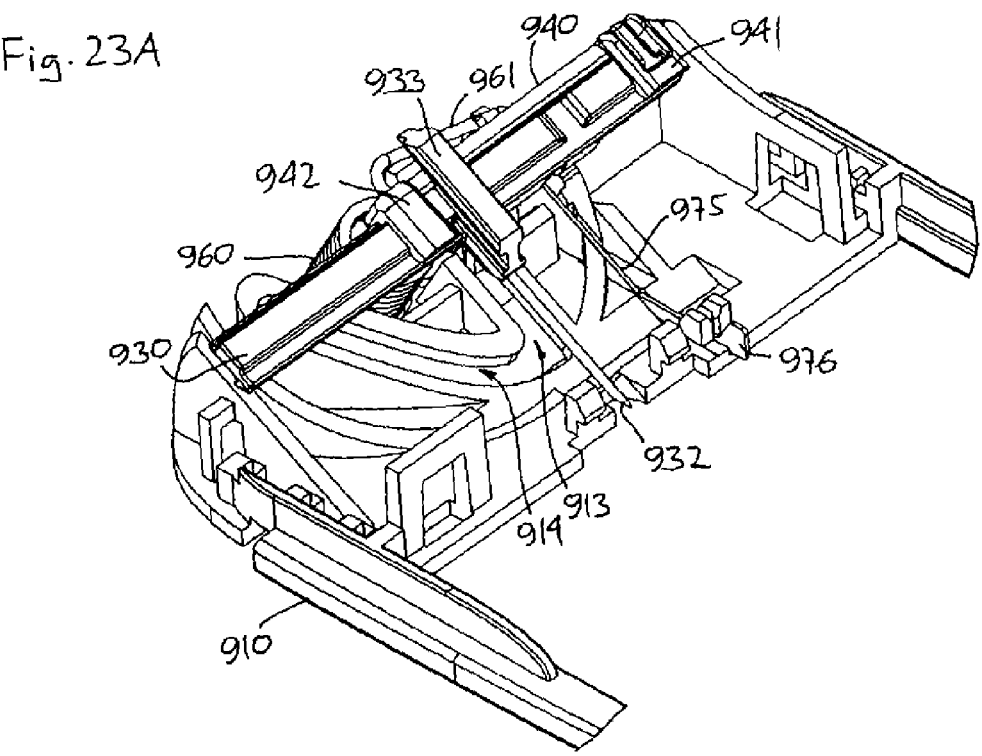
FIGS. 23A-23D show in different actuation states a mechanism for insertion of a cannula.

FIG. 23A shows the assembly in an initial state with the needle holder 930 in a first (or initial) retracted position with the needle correspondingly in its retracted position with the distal pointed end arranged within the housing. The cannula holder is positioned in a right-most position on the needle holder corresponding to its retracted position. The distal portion of the cannula is positioned in the needle with the distal end just within the distal end of the needle, and the intermediate portion is positioned in the channel formed between the needle holder and the cannula holder (see FIG. 24), the cannula being gripped by a flexible arm formed as part of the first gripping member 941.

Figure 23B:
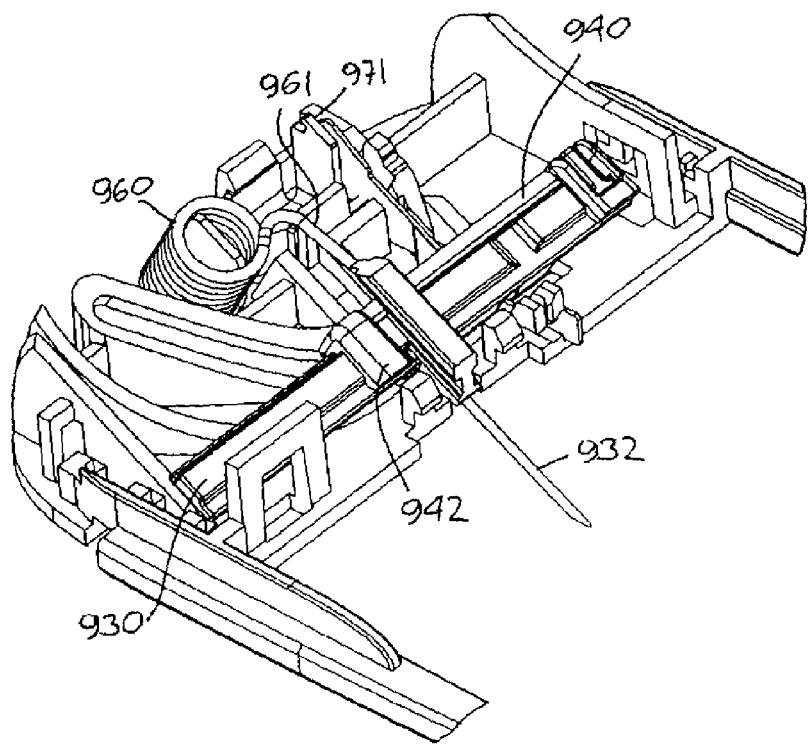

When a pump unit (not shown) is attached to the cannula unit the pump unit engages and pushes the outer end portion 976 of the release member 975, thereby releasing the spring actuator arm 961. The actuator then starts to turn clockwise (as seen in the figure) and engages a rear surface of the needle member pushing it forward to its extended position as seen in FIG. 23B. During this movement the needle holder is guided linearly by engagement with the guide member 921 arranged on an interior surface of the chassis part, whereas the cannula correspondingly is guided linearly to its first extended position by engagement with the first guide groove 913. Thus, during this forward movement, the cannula holder does not move relative to the needle holder.

In this position the needle holder cannot be moved further forward, and as the spring actuator arm continues to turn clockwise it engages the guide member arranged on the lower surface of the cannula holder (not shown, see FIG. 24) thereby starting to move the cannula holder to the left, sliding on the needle holder. At this position the guide member has reached the lower end of the first guide groove (see FIG. 22) and is now moved into the second inclined guide groove where it is moved upwards along the guide groove, thereby being moved further to the left. As the cannula holder is attached to the needle holder, the needle holder is also moved upwards, however, it is guided linearly backwards due to the engagement with the guide member 921. When the cannula holder has reached the upper end of the second guide groove, it has reached its second extended position just as the needle holder has reached its second retracted position (the first and second retracted positions may be the same), just as the cannula holder has reached its second extended position.

As described above, the cannula has a distal portion initially arranged within the needle, an intermediate portion arranged in the channel formed between the cannula and needle holder, and a proximal portion serving as a flexible connection between the moving inserter and the fluid inlet port. As the cannula is attached to the cannula holder corresponding to the proximal end of the intermediate portion, movement to the left of the cannula holder will push the cannula through the channel, around the bend connecting the channel and the needle, and down into the needle. Thus as the cannula holder is moved from its first to its second extended position, the cannula is pushed out through the needle, whereas in the meantime the needle holder with the needle is retracted (see FIG. 23C). In case the cannula and needle are extended respectively retracted at the same speed (this corresponding to the second guide groove being straight and arranged at an angle of 45 degrees relative to the first guide groove) then the distal portion of the extended cannula will not move relative to the housing, whereas the needle will be retracted.

Figure 23C:
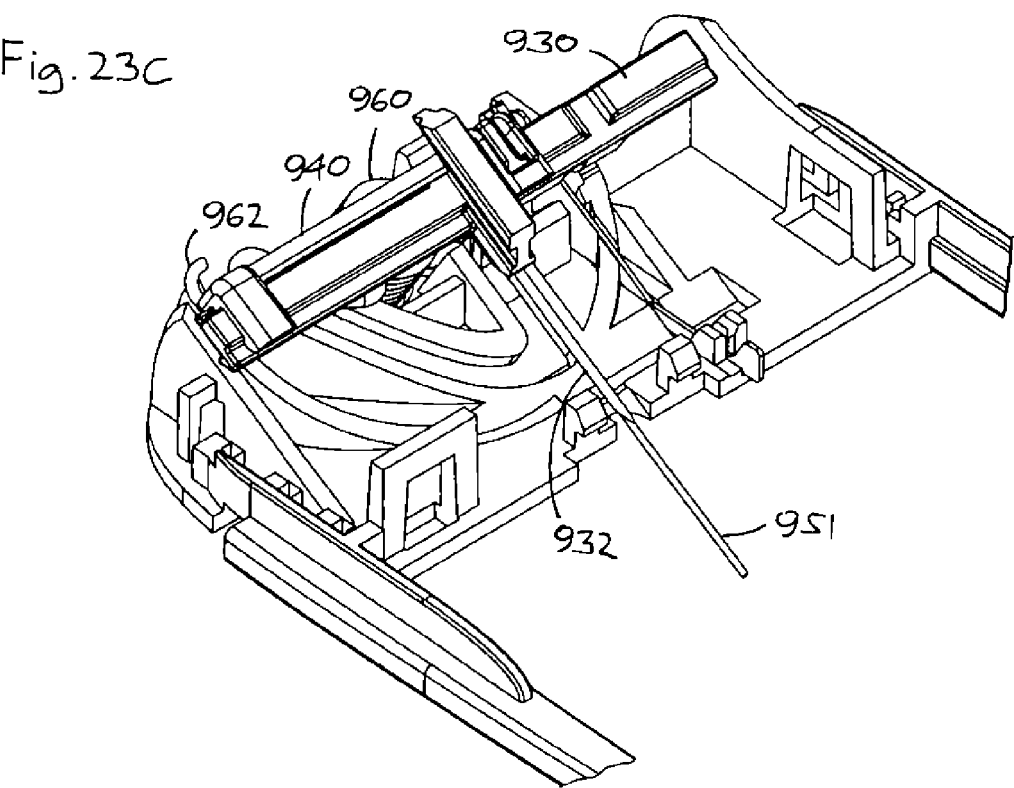
Figure 23D:
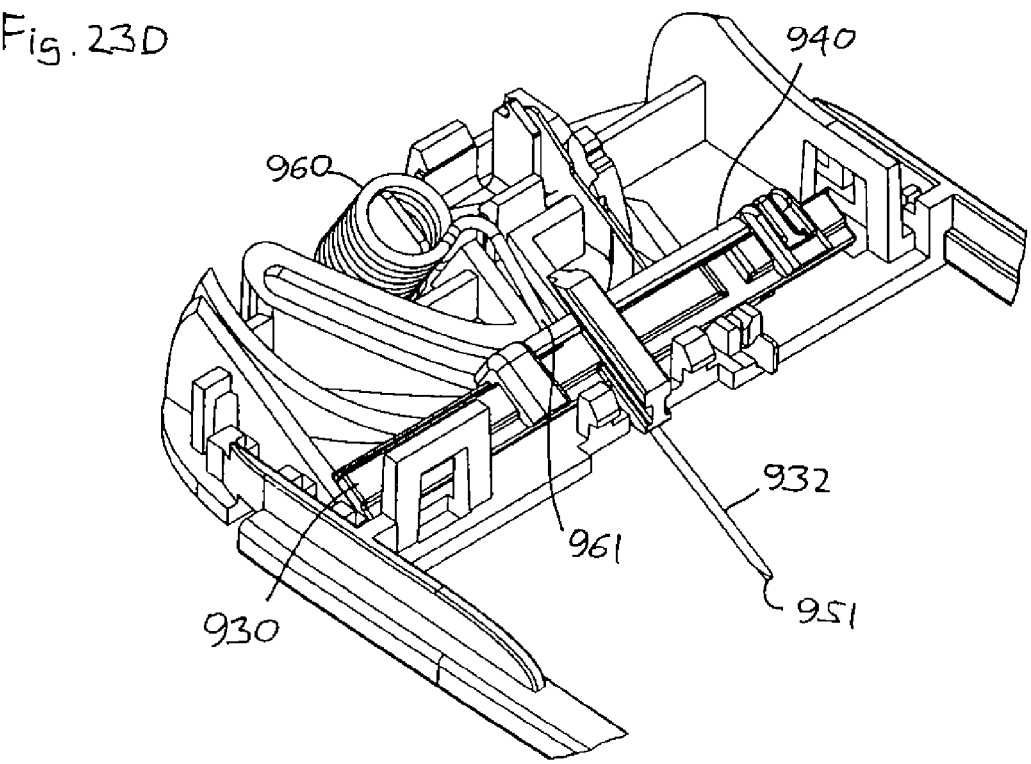

In order to allow the guide member of the cannula holder to properly enter the second guide groove, it may be desirable to connect the two guide grooves with a short groove portion, this providing that the cannula will be extended a little before the needle starts to retract, this as shown in FIG. 23D. Correspondingly, by modifying the configuration of the second guide groove it is possible to retract the cannula a little from its most extended position. The latter may be desirable in order to free a distal cannula opening from any tissue plug formed during insertion.

In FIG. 24 is shown an exploded view of the inserter seen from below, i.e. the needle holder 930 and the cannula holder 940. In the figure the flexible arm 946 for holding the cannula in engagement with the first gripping member 941 can be seen, just as the guide member 945 arranged on the lower surface of the cannula holder can be seen. The needle holder is provided with a longitudinal wall portion 935 adapted for engagement with the spring actuator arm. Between the two holders a channel is formed in which the intermediate portion of the cannula initially is arranged.

Figure 25A:
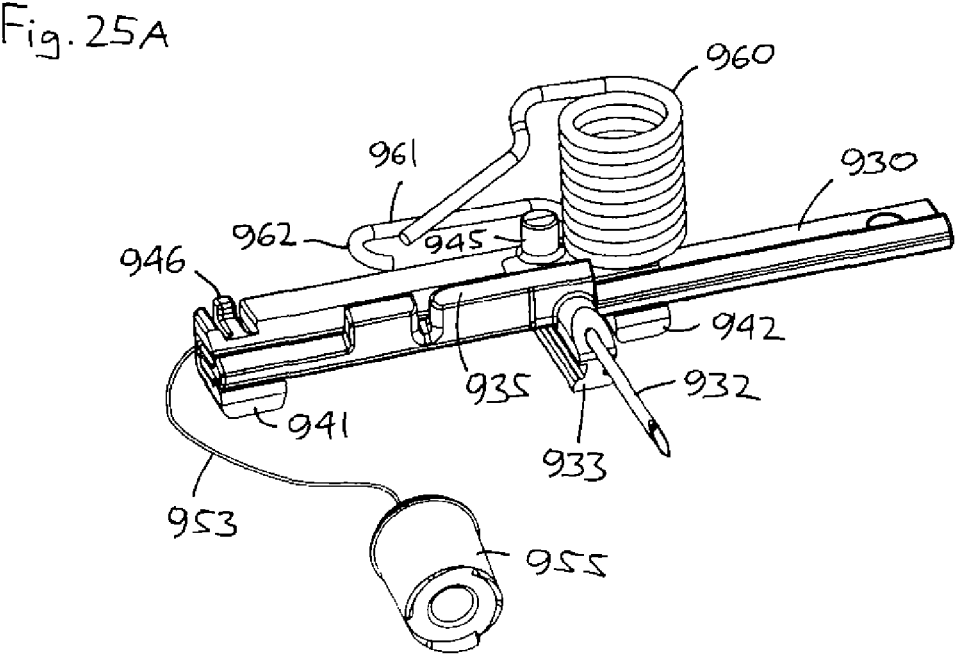
FIGS. 25A-25C show the relationship between the needle holder, the cannula holder, and the spring corresponding to the states shown in FIGS. 23A-23C, FIGS. 26A and 26B show in a non-assembled respectively assembled state a cannula unit and a reservoir unit for a further embodiment of a drug delivery device.
Figure 25B:
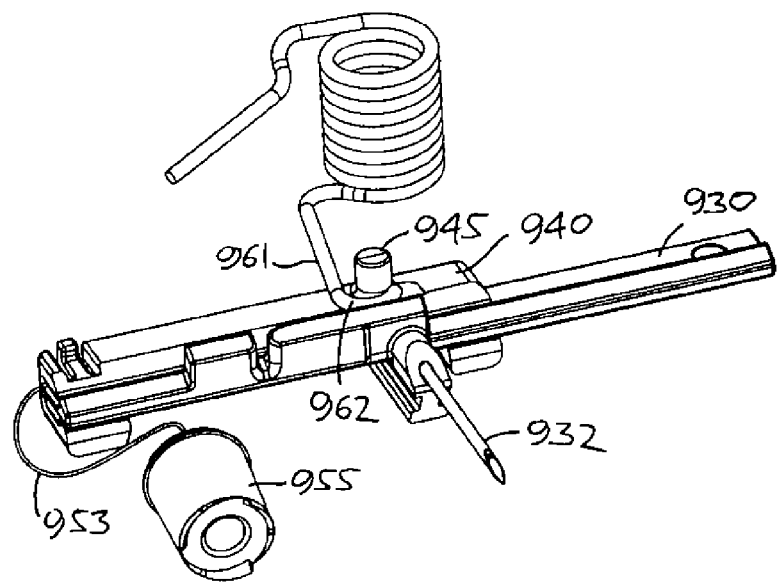
Figure 25C:
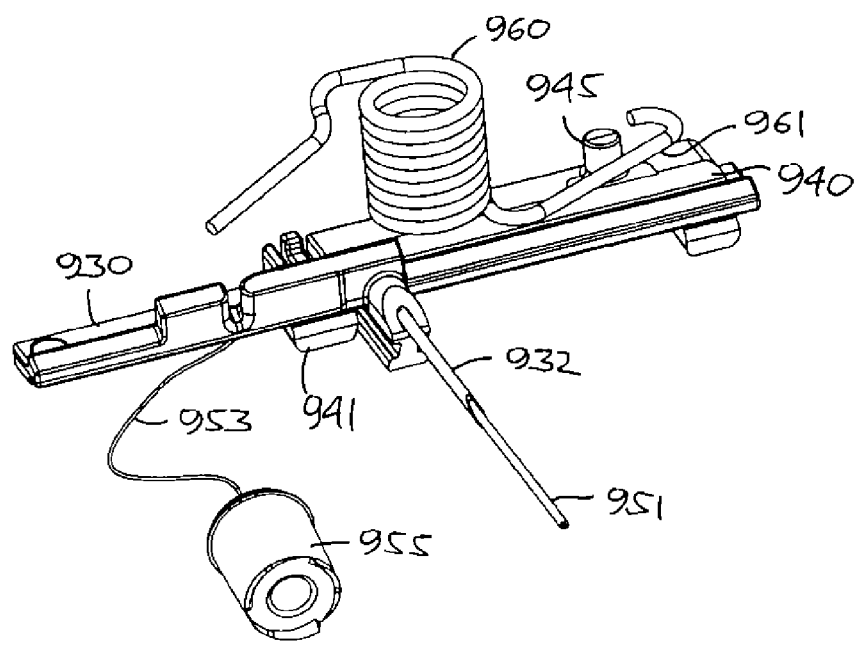

In FIGS. 25A-25C are shown the relationship between the needle holder, the cannula holder, and the spring corresponding to the states shown in FIGS. 23A-23C. The partial assembly is rotated 180 degrees corresponding to the needle axis, and is thus seen from below.

In the initial position the actuator arm 961 is hold in its pre-stressed position in locking engagement with the needle holder (see FIG. 25A). When the spring is released the actuator arm start to turn counter clockwise (as seen in the figure) whereby it engages the wall portion 935 and start to move the needle holder 930 forwards to its extended position (see FIG. 25B). As appears, the curved distal end 962 of the actuator arm allows the arm to slide on the wall. From this position the actuator arm continuous to turn counter clockwise and subsequently engages the guide member 945 on the cannula holder 940 which is then moved to the right (as seen in the figure) to its second extended position and up, guided by the second guide groove, thereby moving the needle holder to its second retracted position (see FIG. 25C). As appears, during the latter movement the guide member 945 slides on the actuator arm. As also appears, during movement of the cannula holder, the free proximal portion 953 of the flexible cannula provides fluid communication between the remaining part of the cannula and the fluid port.

In the above described embodiment, a cannula is guided within a hollow needle, however, other arrangements may be used. For example, the needle may be part-circular (i.e. more than 180 degrees), this providing a smaller cross-sectional area during insertion. Alternatively, the needle and the cannula may be arranged side-by-side with corresponding gripping means provided there between providing that the cannula and needle are only allowed to move longitudinally relative to each other.

In traditional infusion sets a pointed needle is arranged inside a soft cannula, however, although the needle provides the cutting and columnar strength during insertion, the cannula is arranged unprotected against compressive forces in its longitudinal direction, such forces tending to collapse the cannula. Correspondingly, a typical infusion set cannula thus has a relatively thick wall with an outer diameter of 0.7 mm and an inner diameter of 0.4 mm. In contrast, by arranging the soft cannula inside the needle (which is typically made from medial grade stainless steel and thus very rigid), the properties of the needle material can used to provide a much more thin-walled outer tubular structure. For example, a needle with an outer diameter of 0.5 mm and an inner diameter of 0.35 mm may be used, this providing less pain during insertion, just as a thinner soft cannula may be more comfortable to wear. A corresponding cannula will then have an outer diameter of close to 0.35 mm and an inner diameter typically in the 0.15-0.20 mm range. The cannula may be made from e.g. PTFE or FEP.

In the shown embodiment the cannula inserter mechanism is arranged in a cannula unit to be used in combination with a specific pump coupled directly thereto, however, the principles of the inserter mechanism may be used also in a conventional-type infusion set adapted to be connected to an drug delivery pump by a length of tubing. Further, instead of a flexible hollow cannula, a flexible sensor may be introduced. Also, instead of inserting the cannula at an inclined angle relative to a skin surface, a cannula may be inserted perpendicularly, i.e. inclined 90 degrees. Correspondingly, the mechanism may also be arranged to insert the cannula in a direction pointing away from the pump unit to which it is to be attached. In the shown embodiment the cannula is inclined 30 degrees relative to horizontal, however, a preferred range is 20-45 degrees. The less inclined the cannula is arranged, the longer the inserted length in the tissue may be, i.e. corresponding to the protruding length of a transcutaneous device below a plane defined by the mounting surface. For the shown angle of 30 degrees a length of 8 mm is selected, this providing a vertical insertion of approximately 4 mm. For vertical insertion a length of 12 mm or less is preferred for a steel needle, whereas a length of 9 mm or less is preferred for a soft cannula. For a relatively "flat" insertion a length of 20 mm or less is preferred for a soft cannula, typically less than 17 mm.

Figure 26A:
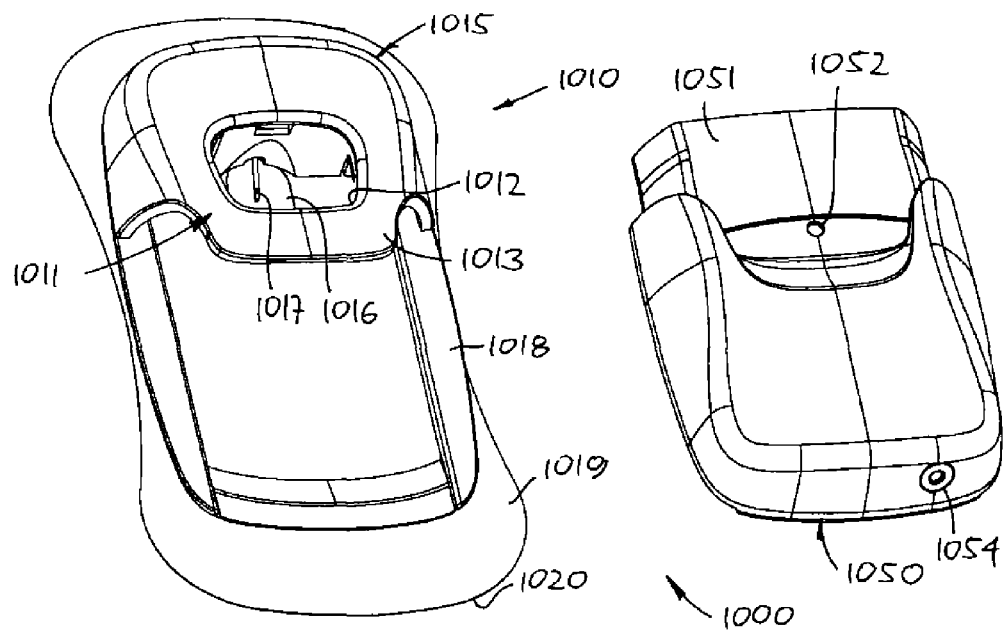

In FIG. 26A is shown an embodiment of a medical device 1000 of the type shown in FIG. 1, comprising a cannula unit 1010 and a thereto mountable pump (or reservoir) unit 1050, however, instead of a needle insertion mechanism as shown in FIG. 7, a cannula inserter mechanism as described with reference to FIGS. 22-25 is used. In the shown embodiment the cannula unit comprises a housing 1015 with a shaft into which a portion 1051 of the pump unit is inserted. The shaft has a lid portion 1011 with an opening 1012, the free end of the lid forming a flexible latch member 1013 with a lower protrusion (not shown) adapted to engage a corresponding depression 1052 in the pump unit, whereby a snap-action coupling is provided when the pump unit is inserted into the shaft of the cannula unit. Also a vent opening 1054 can be seen. The housing 1015 is provided with a pair of opposed legs 1018 and is mounted on top of a flexible sheet member 1019 with a lower adhesive surface 1020 serving as a mounting surface, the sheet member comprising an opening 1016 for the cannula 1017.

Figure 26B:
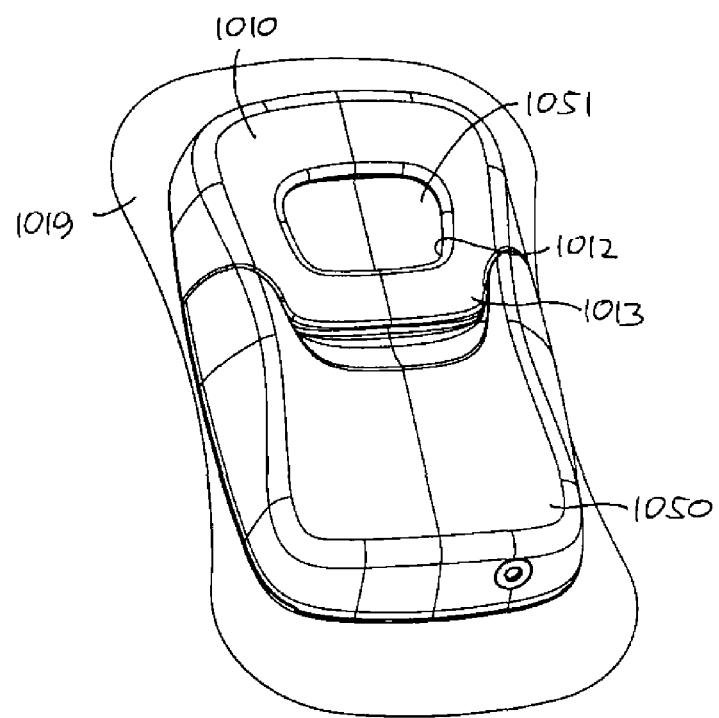

As appears, from the housing of the cannula unit extends a cannula at an inclined angle, the cannula being arranged in such a way that its insertion site through a skin surface can be inspected (in the figure the full cannula can be seen), e.g. just after insertion. In the shown embodiment the opening in the lid provides improved inspectability of the insertion site. When the pump unit is connected to the cannula unit it fully covers and protects the cannula and the insertion site from influences from the outside, e.g. water, dirt and mechanical forces (see FIG. 26B), however, as the pump unit is detachable connected to the cannula unit, it can be released (by lifting the latch member) and withdrawn fully or partly from the cannula unit, this allowing the insertion site to be inspected at any desired point of time. By this arrangement a drug delivery device is provided which has a transcutaneous device, e.g. a soft cannula as shown, which is very well protected during normal use, however, which by fully or partly detachment of the pump unit can be inspected as desired. Indeed, a given device may be formed in such a way that the insertion site can also be inspected, at least to a certain degree, during attachment of the pump, e.g. by corresponding openings or transparent areas, however, the attached pump provides a high degree of protection during use irrespective of the insertion site being fully or partly occluded for inspection during attachment of the pump.

In the shown embodiment an inclined cannula is used, however, in an alternative embodiment a needle mechanism of the type shown in FIG. 7 may be used if the point of insertion was moved closer to the coupling portion of the needle unit, this allowing also such a perpendicularly inserted to be inspected by detaching the pump unit.

Figure 27:
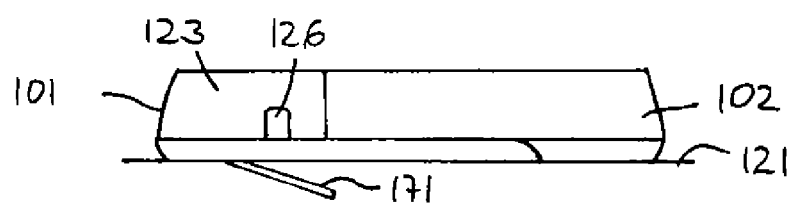
FIG. 27 shows an alternative configuration for the device of FIG. 21A.
Figure 18A:
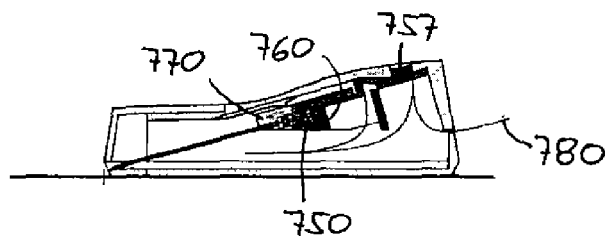
FIGS. 18A-18F show different states of use of the device of FIG. 15.
Figure 18B:
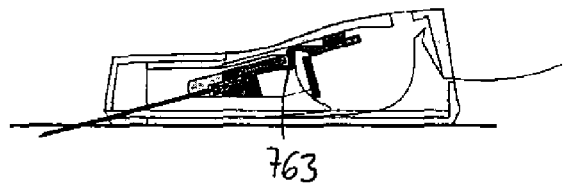
Figure 18C:
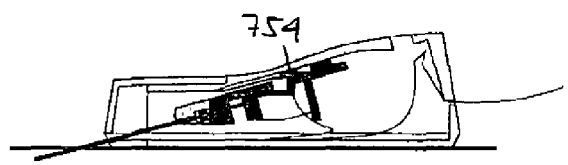
Figure 18D:
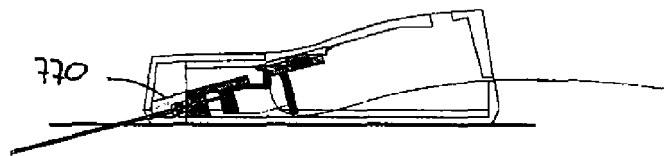
Figure 18E:
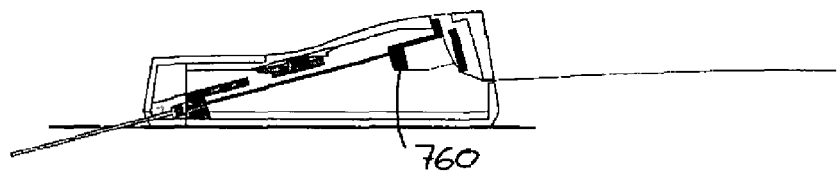
Figure 18F:
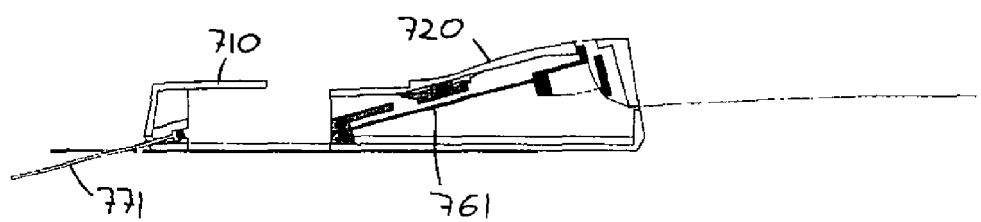

FIG. 27 shows an alternative configuration for the device disclosed in FIG. 21A. As the former embodiment the patch unit 101 comprises a flexible sheet 121 with a lower adhesive surface and an opening for the cannula, a patch housing 123 attached to the upper surface of the sheet and comprising an opening for the cannula, as well as a coupling in the form of two flexible arms 126 allowing a delivery device unit 102 to be attached. However, in contrast to the former embodiment the orientation of the angled cannula 171 has been reversed so that it points essentially in the opposite direction, i.e. towards the attached delivery device unit instead of away from the patch unit. Correspondingly, the opening in the flexible sheet is not peripherally but more centrally located (as indicated with dotted lines 822' in FIG. 21A). As appears, this arrangement allows the point of insertion of the cannula through the skin to be hidden and thus protected by the attached delivery device during normal operation of the assembled device, yet allows the cannula insertion site to be inspected by simply detaching and reattaching the delivery device unit. Further, as the modified inserter is moved towards the delivery device unit this movement may be used to connect the fluid inlet of the cannula with the fluid outlet from the delivery device unit, e.g. by means of a pointed needle connector and a needle penetratable septum arranged on either of the units. As appears, such a reversed arrangement may also be provided for a cannula inserter of the type disclosed with reference to FIGS. 15-18.

Indeed, the concept of a medical device comprising an angled insertable cannula which in its inserted position is covered by a detachable portion of the device can be used in combination with any type of cannula-needle arrangement, not only the embodiments disclosed above. The assembly may also be provided as a unitary device in which an opening may be formed allowing the insertion site to be inspected during use.

Although it is believed that the above-disclosed medical devices can be manufactured in a cost-effective manner, frequent changes of cannula or needle devices, e.g. infusion sets, is one of the cost drivers and poor convenience factors in CSII (continuous subcutaneous insulin infusion) treatment. It is today generally not recommended to wear an infusion set for more than 2 days before changing it, but in practice pump users wear them for a longer time—on average 3.3 days. One of the limiting factors in wear time is that the risk of bacterial growth at the infusion site increases with longer wear times. The preservatives in insulin are anti-bacterial, but since they don't get in touch with the outside of the infusion needle they have no effect on this bacterial growth.

With a porous infusion needle or cannula having a pore size between the molecular size of the preservatives (typically small molecules like meta-cresol and phenol) and the molecular size of insulin (rather large molecules), some of the preservatives will move to the outside of needle where they can reduce bacterial growth and potentially increase the safe wear time of the infusion needle. For a polymeric cannula the entire tube or portions thereof thus can advantageously be made from a polymeric material allowing the preservatives to diffuse from the cannula and into the subcutis. A cannula may also be made from a fibrous material as used in micro tubes for dialysis. For a steel needle laser drilling of micro side openings would allow preservatives together with insulin to diffuse out in the subcutis along the needle (unless the side openings are made so small that they would be an effective barrier to the insulin molecules). The porous portion of the needle may be uniformly porous or it may be adapted to cause weeping at a non-uniform flow rate along the length of the porous portion. A porous portion may e.g. be located at the portion of the needle or cannula intended to cross the skin barrier.

US 2004-0220536, which is hereby incorporated by reference, discloses a surgical needle with a porous distal portion from which a liquid injectate will weep or ooze multidirectionally under injection pressure while the porous distal portion of the needle is inserted into a body surface. More specifically, it is disclosed how a needle or cannula can be provided with pores from which a liquid will ooze. For example, the porous portion of the needle can be fabricated from any of a number of different "open cell" porous materials (i.e., materials in which the pores are interconnecting). For example, a distal portion can be fabricated from a porous sintered metal, such as forms a non-woven matrix of metal fibers selected from such metals as stainless steel, tantalum, elgiloy, nitinol, and the like, and suitable combinations of any two or more thereof. Generally, the metal fibers will have a diameter in the range from about 1.0 micrometer to about 25 micrometer. A non-woven matrix of metal fibers having these desired properties that can be used in manufacture of the porous distal portion of the invention needle is available from the Bekaeart Corporation (Marietta, Ga.), and is sold under the trademark, BEKIPOR® filter medium. A porous portion of the needle can also be fabricated from such porous materials as a porous polymer, such as a porous polyimide, polyethylene, polypropylene, polytetrafluroethylene, and the like. Such porous polymers are disclosed, for example, in U.S. Pat. No. 5,913,856, which is hereby incorporated by reference in its entirety. Alternatively, a porous ceramic can be used, such as is known in the art for use in ceramic filters and separation membranes, or a porous metal (also known as an expanded metal) or carbon, such as is known in the art for use in filters or bone grafts. For example, Mott Corporation (Farmington, Conn.) manufactures porous metals for use in various types of filters. If the porous filter medium is flexible, a porous portion of a needle can be fabricated by wrapping the filter medium, which is available commercially as a flat sheet, one or more times around an axis while creating a hollow central core. The porous portion of the needle can then be fused in fluid-tight fashion (e.g. welded) to a non-porous hollow needle shaft using methods known in the art. To create a porous portion of the needle having decreasing impedance to fluid flow, a porous filter medium or metal mesh having an appropriate porosity gradient can be employed in fabrication of the porous portion. Alternatively, a porous portion can be created from a non-porous material (e.g., a metal) using a cutting laser and techniques known in the art to punch pores into the needle segment (i.e. by a process of laser etching). For example, the nonporous hollow shaft, porous portion, and point of a needle can be fabricated of metal in a single piece, for example, from a conventional hypo tube. In this scenario, a metal-cutting laser is used to create a segment of the needle that has appropriate porosity, for example, a porosity gradient within a portion of the needle to equalize fluid impedance along the length of the porous portion of the needle.

The direct advantage of the above principle is a reduced bacterial growth at the infusion site compared with standard infusion needles. This increases user convenience, since an infusion set can be worn longer before it needs to be replaced—a replacement that can be painful especially for soft infusion needles where a large diameter steel needle is used to guide the soft infusion needle into the skin. Since infusion sets are typically rather expensive, increased wear time will furthermore be cost-attractive to pump users.

In the above-described embodiments a delivery device has been described comprising a flexible reservoir in combination with an example of an expelling means in the form of a membrane pump. However, the reservoir and the expelling means may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

In the following examples of expelling means suitable for use with the present invention will be described, however, these are merely examples, just as the disclosed arrangement of the individual components not necessarily are suitable for direct application in the above shown delivery devices. More specifically, a pump arrangement may comprise a drug-containing cartridge forming a reservoir and having a distal closure member allowing a needle to be connected, and a piston slidingly arranged there within, a flexible toothed piston rod (for example as disclosed in U.S. Pat. No. 6,302,869), an electric motor which via a worm-gear arrangement drives the piston rod to expel drug from the cartridge, the motor being controlled by control means and the energy for the control means and the motor being provided by a battery. The pump may be activated when the needle is inserted or by separate user-actuatable means after the inserter has been detached form the delivery device.

Alternatively a pump arrangement comprises a drug-containing cartridge having distal and proximal closure members and a piston slidingly arranged there within, gas generating means in fluid communication with the interior of the cartridge via conduit for driving the piston to expel drug from the cartridge, the gas generating means being controlled by control means and the energy for the control means and the gas generation being provided by a battery. The pump may be activated as indicated above. A detailed disclosure of such gas generating means for a drug delivery device can be found in e.g. U.S. Pat. No. 5,858,001.

In a further alternative a pump arrangement comprises a drug-containing cartridge having distal and proximal closure members and a piston slidingly arranged there within, an osmotic engine in fluid communication with the interior of the cartridge via conduit for driving the piston to expel drug from the cartridge. The osmotic engine comprises a first rigid reservoir containing a salt-solution and a second collapsible reservoir containing water, the two reservoirs being separated by a semi-permeable membrane. When supplied to the user, the fluid connection between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

In a yet further alternative a pump arrangement comprises a drug-containing flexible reservoir arranged within a rigid fluid-filled secondary reservoir in fluid communication with a primary reservoir through a conduit comprising a flow restrictor. The primary reservoir is in the form of a cartridge with a moveable piston and contains a viscous drive fluid. A spring is arranged to act on the piston to drive fluid from the first to the second reservoir thereby expelling drug from the flexible reservoir when the latter is connected to an infusion needle. The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted or by separate user-actuatable means after the inserter has been detached from the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

Figure 28:
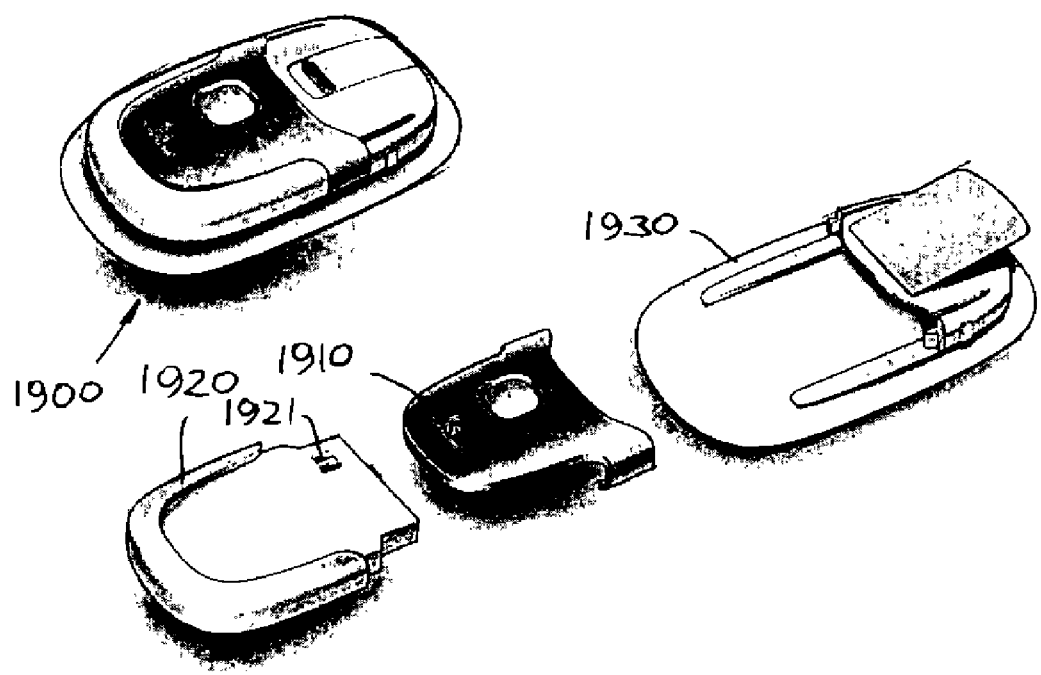
FIG. 28 shows a medical device with a modular reservoir unit.

In FIG. 28 is shown a medical device 1900 corresponding to the embodiment of FIGS. 1-3, however, the reservoir unit has a modular design comprising a "durable" control unit 1910 adapted to be mounted on a reservoir unit 1920 comprising a reservoir and an expelling assembly controllable by the control unit through contacts 1921. The transcutaneous device unit 930 may e.g. be the same as in FIGS. 1-3. The transcutaneous device unit and the reservoir unit comprise mating coupling means (1931) allowing the reservoir unit to be secured to the transcutaneous device unit to provide fluid communication between the reservoir and the transcutaneous device, and the controller unit and the reservoir unit comprise mating coupling means (1917, 1921) allowing the controller unit to be secured to the reservoir unit to control the expelling assembly. The control unit may comprise one or more of the following features: a vibrator, a RF transmitter, a RF receiver, a display, a bolus button 1918 (as shown) or other user input means, a back-up battery, a memory. Further, the control unit may be adapted to provide a fixed flow rate or it may be programmable (e.g. via a remote control) to provide a given rate or a given profile. The different control units may also be used with different reservoir units (e.g. comprising different drugs or different amounts of drugs), or with different needle units (e.g. comprising a needle or a soft cannula). As stated above, the controller may be used as a durable device by the user, however, (simpler) versions of the controller may come pre-attached to a reservoir unit and be used as a means to provide a variety of disposable devices.

Figure 29:
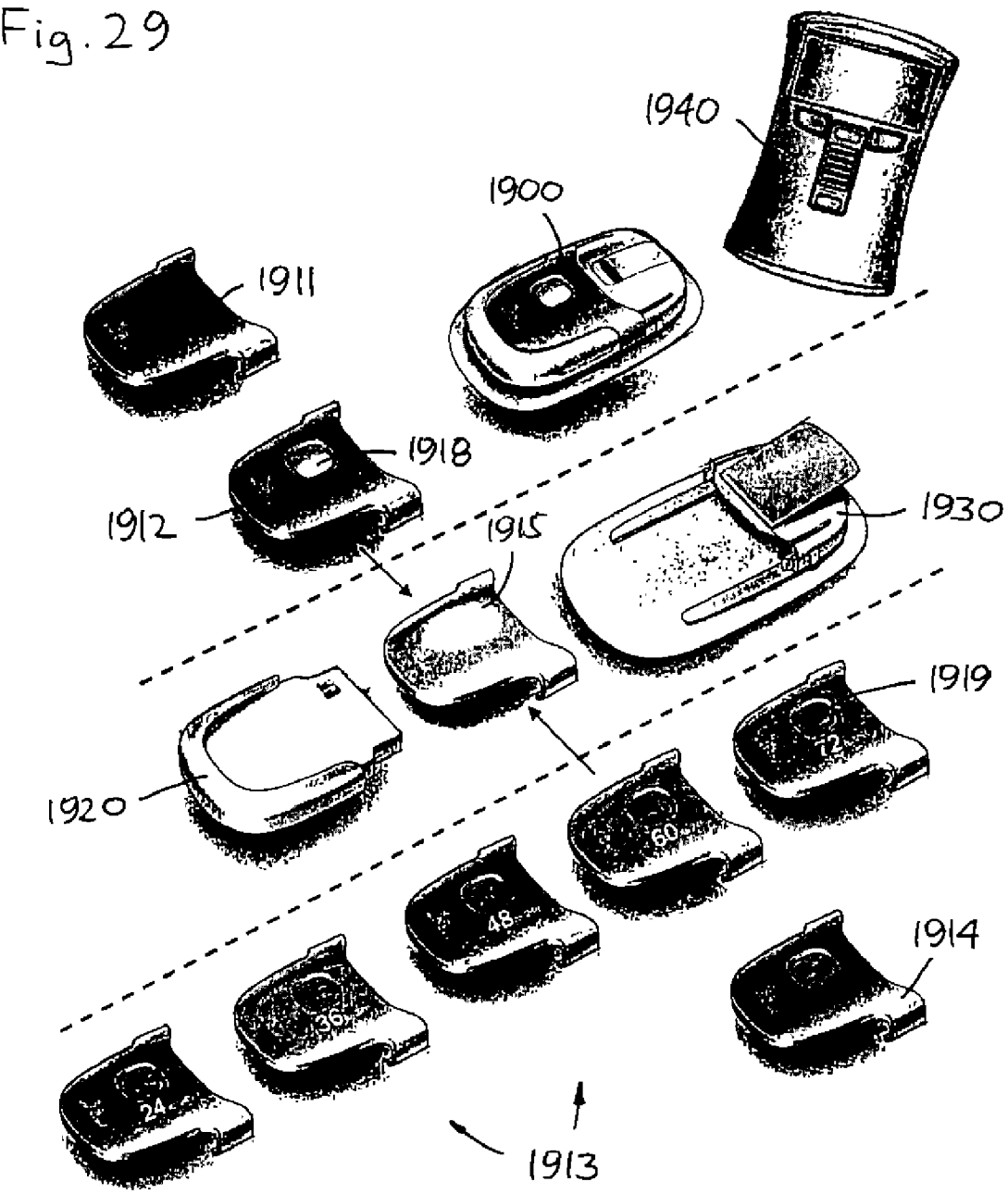
FIG. 29 shows a modular system for a medical device.

FIG. 29 shows a modular system comprising a number of different types of control units in addition to a basic needle patch unit 1930 and a basic reservoir unit 1920. A remote controller 1940 may be used in combination with some of the control units. The control unit may be in the form of a remotely controllable unit 1911 which can only be controlled from a remote controller. A variant 1912 thereof may add a bolus button allowing the user to take a bolus of drug without having to use the remote controller. The control unit may be provided as a variety of preprogrammed control units 1913, each providing a fixed flow rate as indicated on the unit. Such a unit is intended for use without a remote controller and may include a display 1919 as shown. A programmable control unit 1914 may also be provided, this allowing e.g. a medical practitioner to program the control unit for an individual patient. A dummy 1915 represents any of the disclosed control units in combination with a reservoir unit and a needle unit.

In the above disclosure of preferred embodiments of the present invention a system has been described comprising a medical device 1900 used in combination with a remote controller, however, the medical device of the present invention (e.g. a medical device comprising a transcutaneous unit and a reservoir unit or a sensor device comprising a sensor unit and processor unit adapted to transmit and/or process data acquired via the sensor) may also be used in combination with other and further components to form other systems.

For example, the medical device may be used in combination with one or more sensing devices including a sensor adapted to be used in determining a concentration of an analyte of the user. For the treatment of diabetes and to assist in the controlled infusion of insulin, a sensing device may be adapted to measure a blood glucose level in the user. To determine the blood glucose level of a person suffering from diabetes, two types of devices may be used.

The traditional blood glucose meter (BGM) is normally used manually a given number of times each day and is based on the application of a small amount of blood to a test strip 1821, 1831 (see FIG. 30A) which is then subsequently placed in the BGM which then supplies a blood glucose value on its display. Traditionally this value was used to check that the blood glucose value was within a desired range, however, it may also be entered into a bolus calculator (also termed a bolus estimator) which will then e.g. recommend a correction bolus to be injected or infused. An early example of a bolus calculator is the "B-D Insulin Dosage Computer" which can also be used to calculate a meal bolus on the basis of user-entered meal information. A bolus calculator may also be incorporated into a drug delivery device, e.g. as shown in U.S. Pat. Nos. 5,665,065 and 6,554,798 or US 2004/0068230, or it may be incorporated into a remote controller for a drug delivery device as shown e.g. in US 2005/0022274 or US 2005/0065760 (also showing that a BGM may be incorporated in the remote controller), which are hereby all incorporated by reference. It is considered that the general design of a remote controller and the corresponding aspects of a controlled device are well known to the skilled person, however, for a more detailed description of the circuitry necessary to provide the desired functionality of the present invention reference is made to US 2003/0065308, which are hereby all incorporated by reference.

In addition to a BGM blood glucose values may also be provided using a continuous blood glucose meter (CGM) which provides continuous or quasi-continuous (e.g. every five minute) blood glucose values. A CGM may be implantable or non-implantable based on e.g. a transcutaneous sensor, a non-transcutaneous sensor or micro-dialysis using a small cannula, and often comprises an external portion attached to the skin of the user by adhesive, the sensor and the external portion forming a sensor unit. The external portion comprises sensor electronics adapted to process and/or transmit the "raw" sensor data supplied from the sensor being indicative of the determined concentration of the analyte in the user. For example, the sensor data may be transmitted to a further unit by wire or wirelessly for further processing, or they may be processed in the external portion of the sensor unit to determine a concentration of the analyte (e.g. glucose) in the user. These values may then be displayed by the sensor unit and/or transmitted to a further unit by wire or wirelessly, where it can be displayed, stored and/or used for further processing. The values supplied from or via the CGM may be used by a bolus estimator for calculating an estimated amount of drug (e.g. insulin) to be infused into the body of the user based upon the received data or they may be used in a closed-loop system for adjusting a basal rate infusion of a drug. Preferably, also BGM values are supplied to the bolus estimator or system in order to adjust for any sensor drift. The bolus or closed-loop calculator may be part of a drug delivery device or it may be part of a remote control unit from which commands are then transmitted to the delivery device. In the following and with reference to FIGS. 30A-30C a number of exemplary systems 1800, 1801, 1802 will be described using one or more sensor devices for determining blood glucose, however, other types of sensors for determining the concentration of other analytes may be used. In the below examples the remote control unit is used to collect BGM/CGM data and to calculate and transmit bolus instructions to the delivery device, however, the remote control unit is preferably used as the main user interface between the delivery device and the user allowing the user to e.g. program the delivery device with a given basal rate profile and to change such a profile, to program a bolus amount and the form thereof, and receive information from the delivery device (e.g. by detection of an occlusion). The remote unit may also serve as a storage device for storing information in respect of infusion history (e.g. basal rate and bolus infusions), alarms, personal information (e.g. for preferred types of meals to be used in bolus calculations) and to send data to an external device such as a PC or expert system.

EXAMPLE 1

Figure 30A:
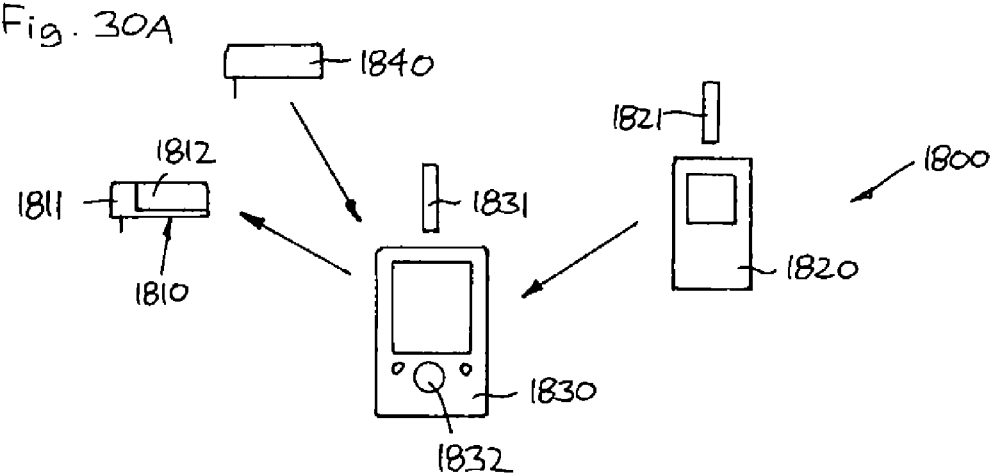
FIGS. 30A-30C show infusion systems comprising delivery device, analyte sensor and remote control unit.
Figure 30B:
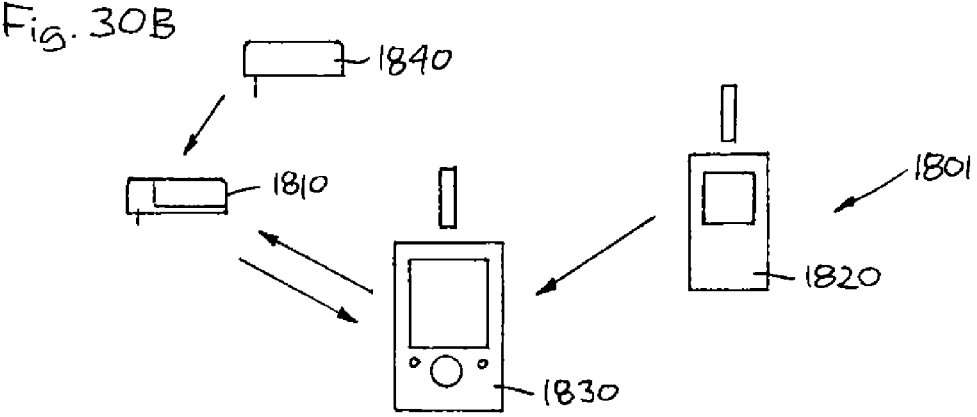
Figure 30C:
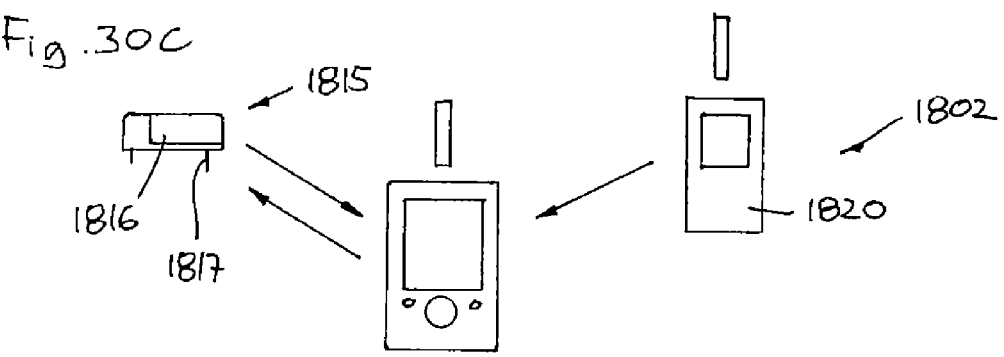

A medical drug delivery device 1810 comprising a transcutaneous device unit 1811 and a reservoir unit 1812 as disclosed above is provided in combination with a BGM 1820 and a wireless remote control unit 1830 comprising a processor and an infusion calculator, thereby forming system 1800. On basis of blood glucose values and/or values entered into the system by a user via a keyboard 1831 (e.g. in respect of a meal) a bolus is calculated and when accepted by the user it is transmitted to the drug delivery device which then infuses the bolus. The BGM data may be entered into the remote unit manually, they may be transmitted from the BGM to the remote unit or the BGM may alternatively be integrated into the remote unit. The CGM shown in FIG. 30A is not used in this system.

EXAMPLE 2

A medical drug delivery device 1810 comprising a transcutaneous device unit and a reservoir unit as disclosed above is provided in combination with a BGM 1820, a CGM 1840 and a wireless remote control unit 1830 comprising a processor and an infusion calculator, thereby forming system 1800. Data is transmitted from the CGM to the remote unit where they are used in conjunction with BGM data and optionally other data to calculate a bolus or a change in an actual basal rate infusion profile. When a bolus or profile change is calculated it may be transmitted automatically to the drug delivery device (closed loop) or it may be displayed to the user for acceptance (open loop). The BGM data may be entered into the remote unit manually, they may be transmitted from the BGM to the remote unit or the BGM may be integrated into the remote unit. The data supplied from the CGM and BGM may be raw sensor data or processed data representing a blood glucose value.

EXAMPLE 3

A medical drug delivery device 1810 comprising a transcutaneous device unit and a reservoir unit as disclosed above is provided in combination with a BGM 1820, a CGM 1840 and a wireless remote control unit 1830 comprising a processor and an infusion calculator, thereby forming system 1801. Data is transmitted from the CGM to the delivery device and from the delivery device to the remote unit. This arrangement may be advantageous when the distance between the sensor unit and the delivery device is small and when the delivery device is provided with a memory, this allowing CGM data to be transmitted to the remote unit "in bulk", e.g. every hour, this improving energy efficiency. Otherwise the system may be provided and used as described in example 2.

EXAMPLE 4

A medical drug delivery device 1815 comprising a transcutaneous device unit and a reservoir unit as disclosed above is provided in combination with a BGM 1820, a CGM 1816 and a wireless remote control unit 1830 comprising an infusion calculator, thereby forming system 1802. In contrast to examples 2 and 3, the CGM is formed integrally with the delivery device. Advantageously a transcutaneous sensor 1817 is formed as part of the transcutaneous device unit and the sensor electronics adapted to process and/or transmit the sensor data is formed as part of the reservoir unit. The sensor may be replaced together with the transcutaneous device or independently thereof. Otherwise the system may be provided and used as described in example 3.

EXAMPLE 5

A medical drug delivery device comprising a transcutaneous device unit and a reservoir unit as disclosed above is provided in combination with a BGM and/or a CGM, the reservoir unit being adapted to receive BGM/CGM data (e.g. wirelessly) and comprising a bolus calculator. The bolus calculator may use the BGM/CGM to calculate a recommendation as described above in examples 1 or 2, or it may calculate and implement a bolus or change of infusion profile.

Figure 31A:
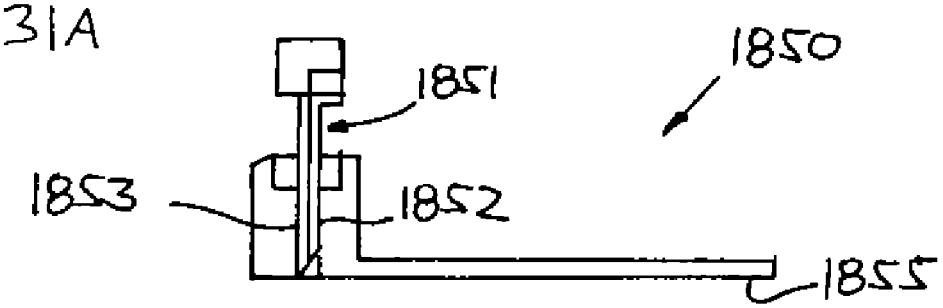
FIGS. 31A and 31B show a modular medical sensor device in different stages.
Figure 31B:
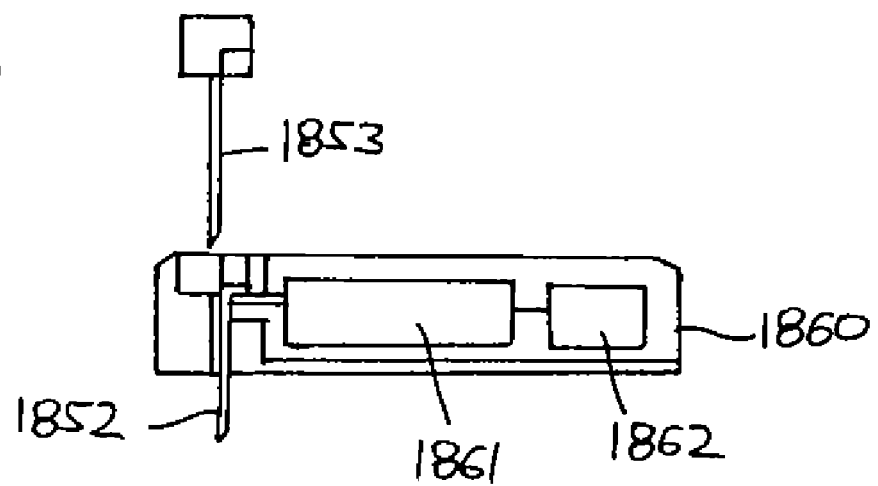

In the above examples, when a separate medical sensor device is used (e.g. a CGM sensor), such a sensor device may comprise a sensor unit and a processor unit, the sensor unit comprising: a transcutaneous sensor device, a mounting surface adapted for application to the skin of the subject, the processor unit comprising: a processor adapted to transmit and/or process data acquired via the sensor, wherein the sensor unit and the processor unit are adapted to be secured to each other in a situation of use to thereby form a unitary device. Turning to FIGS. 31A and 31B a sensor unit 1850 is shown, comprising a transcutaneous device 1851 in the form of a needle-formed sensor 1852 in combination with an insertion needle 1853, and a mounting surface 1855 adapted for application to the skin of the subject. After the sensor unit has been placed on a skin surface (see FIG. 31A) the combined transcutaneous device is inserted transcutaneously by the user where after the insertion needle is withdrawn, this leaving the sensor in place (see FIG. 31B. Finally the user attaches the process unit 1860 thereby establishing contact between the needle sensor and the circuitry of the process unit. The process unit comprises a processor 1861 adapted to transmit and/or process data acquired via the sensor device as well as a power source 1862. A further example of sensor insertion can be found in U.S. Pat. Nos. 5,568,806 and 6,809,653, which are hereby incorporated by reference, also disclosing technical information in respect of communication between a medical sensor and an external device.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical device, comprising a transcutaneous device unit and a process unit,
   a) the transcutaneous device unit comprising:
      a mounting surface configured for application to the skin of a subject,
      a transcutaneous device comprising a distal end configured to be inserted through the skin of the subject, the distal end being moveable between an initial position in which the distal end is retracted relative to the mounting surface, and an extended position in which the distal end projects relative to the mounting surface,
   b) the process unit comprising:
      a process assembly configured to cooperate with the transcutaneous device,
   wherein the transcutaneous device is a combined transcutaneous device comprising a sensor, and the process assembly comprises a processor configured to transmit and/or process data acquired via the sensor,
   wherein the process assembly comprises a reservoir configured to contain a fluid drug, an expelling assembly configured for cooperation with the reservoir to expel fluid drug out of the reservoir and through the skin of the subject via the combined transcutaneous device, and
   wherein the transcutaneous device unit and the process unit are configured to be secured to each other to form a unitary device.

2. A medical device as in claim 1, wherein the transcutaneous device is provided in combination with a pointed insertion needle being retractable relative to the transcutaneous device.

3. A medical device as in claim 2, wherein the insertion needle is a hollow needle arranged coaxially with and outside the transcutaneous device and being axially moveable relative thereto, the needle comprising a distal portion adapted to penetrate the skin of the subject, wherein the medical device is transformable between:
   a first state in which the transcutaneous device and the needle are retracted relative to the mounting surface,
   a second state in which the transcutaneous device and the needle are extended relative to the mounting surface with the distal end of the needle projecting relative to the distal portion of the transcutaneous device thereby allowing the transcutaneous device to be introduced through the skin of the subject, and
   a third state in which the distal end of the needle is retracted relative to the distal portion of the transcutaneous device.

4. A medical device as defined in claim 1, wherein the transcutaneous device unit comprises an actuator configured to move the distal end of the transcutaneous device between the initial and the extended position.

5. A medical device as in claim 1, wherein the process unit is configured to be releasably coupled to the transcutaneous device unit thereby, in a situation of use, substantially covering an introduction site of the transcutaneous device through the skin, and wherein at least partial removal of the process unit from the transcutaneous device unit at least partially uncovers the introduction site.

6. A medical device as in claim 1, wherein the transcutaneous device unit comprises a housing portion to which the transcutaneous device is mounted, and a flexible sheet member provided with an adhesive layer on its lower surface, the adhesive layer being configured to attach the transcutaneous device unit to the skin of the subject.

7. A system comprising:
a medical device as in claim 1, and a remote control unit comprising a processor, the medical device and the remote control unit being adapted to transmit data therebetween.

8. A system as in claim 7, wherein the remote control unit is configured to receive externally supplied values and to calculate a bolus amount of drug to be infused based upon the externally supplied values.

9. A system as in claim 8, wherein the remote control unit is configured to calculate a bolus amount of drug to be infused based upon externally supplied values representing material to be ingested by the body of the subject.

10. A system as in claim 8, further comprising a first analyte sensor device configured to provide data indicative of a concentration of the first analyte in the user, the remote control unit comprising an infusion calculator for calculating a bolus or infusion rate on the basis of data supplied by the first analyte sensor.

11. A system as in claim 10, further comprising a second analyte sensor device configured to provide data indicative of a concentration of the second analyte in the user, the remote control unit comprising an infusion calculator for calculating a bolus or infusion rate on the basis of data supplied by the first and second analyte sensors.

12. A system as in claim 11, wherein the first and second analytes are blood glucose, the first analyte sensor is a BGM, the second analyte sensor is a CGM, and the remote control unit is adapted to calculate an amount or infusion rate of insulin.

* * * * *

UNITED STATES PATENT AND TRADEMARK OFFICE
CERTIFICATE OF CORRECTION

| | | |
|---|---|---|
| PATENT NO. | : 8,298,172 B2 | Page 1 of 1 |
| APPLICATION NO. | : 11/911213 | |
| DATED | : October 30, 2012 | |
| INVENTOR(S) | : Nielsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 296 days.

Signed and Sealed this
Twenty-sixth Day of August, 2014

Michelle K. Lee
*Deputy Director of the United States Patent and Trademark Office*